US006859760B2

(12) United States Patent
Dorough

(10) Patent No.: US 6,859,760 B2
(45) Date of Patent: Feb. 22, 2005

(54) REMOTE SEMICONDUCTOR MICROSCOPY

(75) Inventor: Michael J. Dorough, Meridian, ID (US)

(73) Assignee: Micron Technology, Inc., Boise, ID (US)

( * ) Notice: Subject to any disclaimer, the term of this patent is extended or adjusted under 35 U.S.C. 154(b) by 137 days.

(21) Appl. No.: 10/441,703

(22) Filed: May 20, 2003

(65) Prior Publication Data

US 2003/0208340 A1 Nov. 6, 2003

Related U.S. Application Data

(62) Division of application No. 10/118,844, filed on Apr. 9, 2002, now Pat. No. 6,567,770, which is a division of application No. 09/298,502, filed on Apr. 23, 1999, now Pat. No. 6,370,487.

(60) Provisional application No. 60/103,669, filed on Oct. 9, 1998, and provisional application No. 60/082,846, filed on Apr. 23, 1998.

(51) Int. Cl.[7] .............................................. G06F 15/16
(52) U.S. Cl. .................. 702/188; 702/33; 702/189; 702/122; 702/121; 702/123
(58) Field of Search ........................... 702/33–36, 40, 702/58, 59, 81–84, 117–119, 121–124, 126, 170, 172, 183, 184, 185, 188, 189, 198, FOR 103–104, FOR 123, FOR 125, FOR 131, FOR 134–135, FOR 137, FOR 148, FOR 170–171; 382/141, 144, 145, 147, 149, 150, 155, 159; 356/237, 394; 348/87, 101, 125, 126; 709/200–203, 206, 217–219, 227–229, 231, 232, 236, 237, 245; 707/10, 200–203; 713/201, 202

(56) References Cited

U.S. PATENT DOCUMENTS

| | | | |
|---|---|---|---|
| 4,673,988 A | 6/1987 | Jansson et al. ........... 3588/280 |
| 4,902,967 A | 2/1990 | Flesner ..................... 324/158 |
| 4,916,640 A | 4/1990 | Gasperi et al. ............ 364/521 |
| 5,086,477 A | * 2/1992 | Yu et al. .................... 382/145 |
| 5,140,164 A | 8/1992 | Talbot et al. ............. 250/392.2 |
| 5,199,054 A | 3/1993 | Adams et al. .............. 378/21 |
| 5,301,240 A | 4/1994 | Stockum et al. ............ 382/1 |
| 5,351,129 A | 9/1994 | Lai ........................... 348/584 |
| 5,566,877 A | * 10/1996 | McCormack ............... 228/105 |
| 5,586,058 A | 12/1996 | Aloni et al. ................ 364/552 |
| 5,696,835 A | 12/1997 | Hennessey et al. ........ 382/141 |
| 5,741,171 A | * 4/1998 | Sarfaty et al. ................ 451/6 |
| 5,761,064 A | 6/1998 | La et al. ................. 364/468.17 |
| 5,818,637 A | 10/1998 | Hoover et al. .............. 359/381 |
| 5,875,258 A | 2/1999 | Ortyn et al. ................ 382/133 |

(List continued on next page.)

OTHER PUBLICATIONS

"Advanced Streaming Format", Microsoft Corporation, http://www.microsoft.com/asf/whitepr/asfwp.htm,(Jan. 1998),pp. 1–11.

(List continued on next page.)

Primary Examiner—Carol S. Tsai
(74) Attorney, Agent, or Firm—Scwegman, Lundberg, Woessner & Kluth, P.A.

(57) ABSTRACT

A method and apparatus are described for remote semiconductor microscopy whereby video signals are broadcast from one or more microscopes to remote viewers. A live video signal is broadcast from the microscope over a network to remote personal computers located in the offices of process engineers. The office-based process engineers are provided real-time, or substantially real-time, views of a wafer, including peripheral views of the wafer outside cell array boundaries. The process engineer, in his office, can direct a technician, operating the microscope in the clean room complex, to display a desired cell region-of-interest with the microscope. As a result, the process engineers can more efficiently collaborate to solve process problems or even develop new process techniques.

33 Claims, 21 Drawing Sheets

U.S. PATENT DOCUMENTS

| | | | |
|---|---|---|---|
| 5,877,497 A | | 3/1999 | Binnig et al. ............... 250/306 |
| 5,943,437 A | * | 8/1999 | Sumie et al. ............... 382/149 |
| 5,978,071 A | | 11/1999 | Miyajima et al. ............. 355/53 |
| 5,986,262 A | | 11/1999 | Volcker ...................... 250/306 |
| 5,995,670 A | | 11/1999 | Zabinsky .................... 382/242 |
| 6,025,827 A | | 2/2000 | Bullock et al. ............. 345/115 |
| 6,026,230 A | | 2/2000 | Lin et al. ............... 395/500.34 |
| 6,043,882 A | * | 3/2000 | De Wolf et al. ............ 356/326 |
| 6,044,131 A | | 3/2000 | McEvoy et al. ............ 378/162 |
| 6,061,057 A | | 5/2000 | Knowlton et al. .......... 345/335 |
| 6,088,018 A | | 7/2000 | DeLeeuw et al. ........... 345/156 |
| 6,093,019 A | | 7/2000 | Morandi et al. .............. 433/29 |
| 6,122,562 A | * | 9/2000 | Kinney et al. .............. 700/121 |
| 6,128,073 A | | 10/2000 | Henzler et al. ............... 356/72 |
| 6,130,967 A | | 10/2000 | Lee et al. ................... 382/302 |
| 6,144,762 A | | 11/2000 | Brooks ....................... 382/154 |
| 6,147,797 A | * | 11/2000 | Lee ............................. 359/363 |
| 6,171,874 B1 | | 1/2001 | Steffan et al. ................ 438/14 |
| 6,177,955 B1 | * | 1/2001 | Downen et al. ............ 348/189 |
| 6,246,787 B1 | * | 6/2001 | Hennessey et al. ......... 382/141 |
| 6,268,957 B1 | * | 7/2001 | Hoover et al. ............... 359/368 |
| 6,275,922 B1 | | 8/2001 | Bertsch ........................ 712/36 |
| 6,287,020 B1 | * | 9/2001 | Osaka et al. ................... 385/96 |
| 6,292,582 B1 | * | 9/2001 | Lin et al. .................... 382/149 |
| 6,313,452 B1 | | 11/2001 | Paragano et al. ........ 250/201.3 |
| 6,314,379 B1 | | 11/2001 | Hu et al. ....................... 702/81 |
| 6,327,002 B1 | | 12/2001 | Rinaldi et al. .............. 348/554 |
| 6,353,848 B1 | * | 3/2002 | Morris ....................... 709/203 |
| 6,400,441 B1 | | 6/2002 | Nishi et al. ................... 355/53 |
| 6,405,153 B1 | | 6/2002 | Fiekowsky .................. 702/172 |
| 2002/0089349 A1 | | 7/2002 | Barbier et al. ................ 326/39 |

OTHER PUBLICATIONS

Grimes, G. J., "Remote Microscopy for Hi Res Real–Time Interactive Pathology", *Advanced Imaging*, (1997),p. 12,14, 16.

Lampso, B. W. et al., "Experience with Processes and Monitors in Mesa", *Communications of the ACM, 23(2)*, (1980),pp. 105–117.

\* cited by examiner

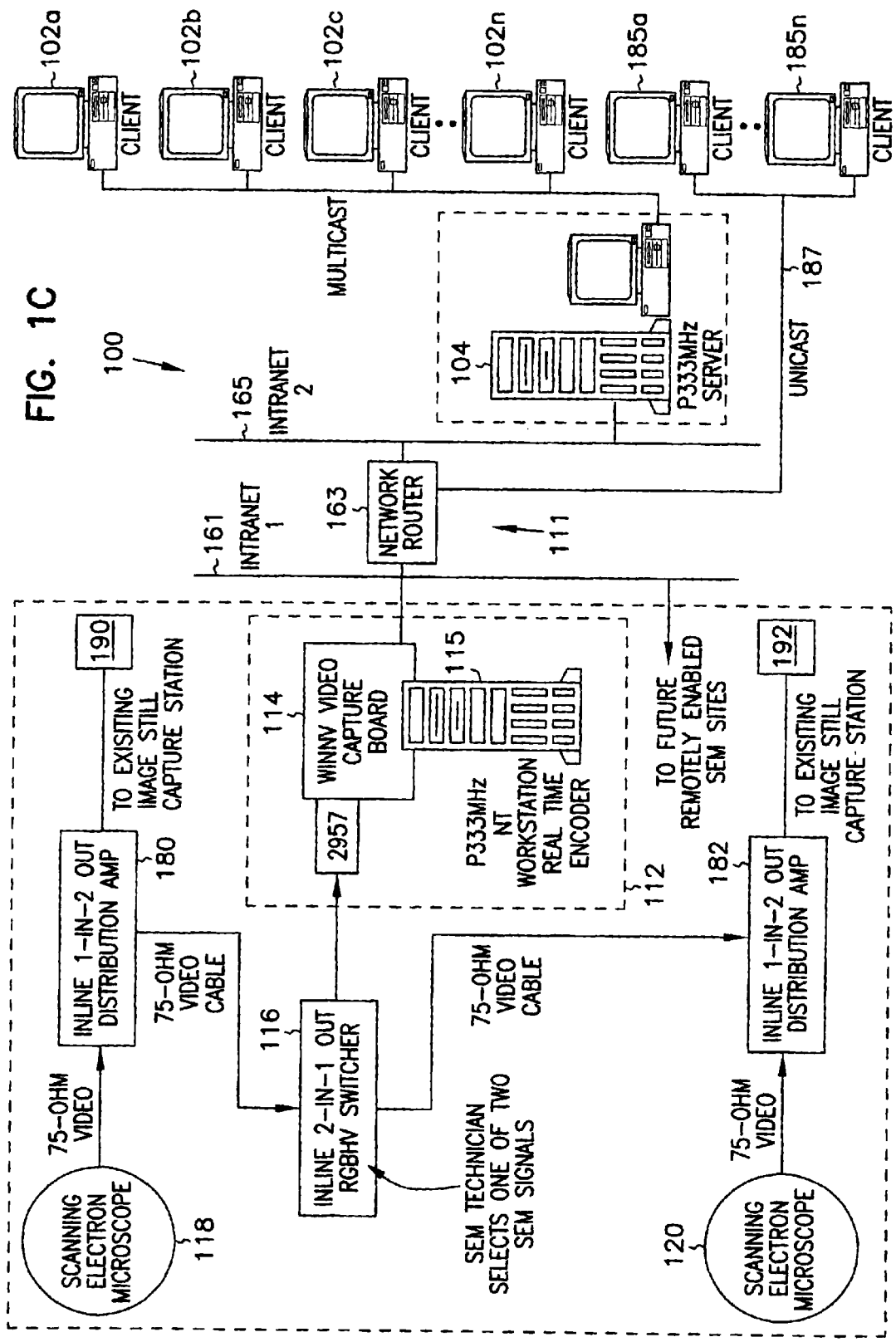

NTSC COMPOSITE VIDEO SIGNAL FOR 75% AMPLITUDE, 100% SATURATED EIA COLOR BARS. INDICATED VIDEO LEVELS ARE 8-BIT VALUES AFTER DC RESTORATION AND OFF SET DURING SYNCH TIP.

ProduceFrameThread

```
PRODUCE

UINT ProducerFrameThread::produceFrame(LPVOID pThread)
{
    ProducerFrameThread* pCFT= (ProducerFrameThread*)pThread;
    if (pCFT)
    {
        // if terminate event is signaled then wait
        DWORD dwEvent;
        while((dwEvent=WaitForMultipleObjects(2,hLifetime,TRUE,0))==WAIT_TIMEOUT)
        {
            pCFT->pHBFM->StartCompressing();
            pCFT->pFrameGrabber->GrabFrame();
            pCFT->pHBFM->StopCompressing;
        }
    }
    return 0; //exit thread
}
```

Fig. 6C

ConsumerFrameThread

CONSUME

```
UINT ConsumerFrameThread::consumeFrame(LPVOID pThread)
{
    ConsumerFrameThread* pCFT= (ConsumerFrameThread*)pThread;
    if (pCFT)
    {
        // if terminate event is signaled then wait
        DWORD dwEvent;
        while((dwEvent=WaitForMultipleObjects(2,hLifetime,TRUE,0))==WAIT_TIMEOUT)
        {
            pCFT->pHBFM->StartCompressing();
            pCFT->pCODEC->CompressFrame();
            pCFT->pHBFM->StopCompressing;
        }
    }
    return 0; //exit thread
}
```

Fig. 6D

Condition

```
Condition(Monitor*pMon;
{
    pHBFM=pMon;
    numberOfBlocks=0;
    pConditionQueue=new Queue;
}
```

PRECONDITION

WAITING

```
Wait
{
    //Create a BinarySemaphore to block thread
    BinarySemaphore *pSemaphore=new BinarySemaphore();

//Add this BinarySemaphore to Queue using FIFO
    pConditionQueue->AddFIFO((void*) pSemaphore);
    semaphoreCount++;

//If there are any waiting threads, then release first
    //thread in queue.
    If (pHBFM->numberOfWaitingThreads)
    {
        Semaphore *pitem=(Semaphore*)
        pHBFM->pEntryQueue->GetHead()
        if (pitem)
        {
            //Permit thread to run in
            //HostBasedFrameMonitor
            pitem->Unblock();
        }
    }
    else
    {
        //Release ownership of HostBasedFrameMonitor
        pHBFM->ReleaseOwnership();
    }
    //Block the new thread and make it wait to be
    //signaled
    pSemaphore->Block();
    //We're back from block and now thread owns
    //HostBasedFrameMonitor
    numberOfBlocks--;
    delete pSemaphore;
};
```

Fig. 8B-1

| Queue |
|---|
| semaphoreItemCount |
| AddFIFO |
| AddLIFO |
| GetHead |
| IsEmpty |

Fig. 9A

| BinarySemaphore |
|---|
| hSemaphore |
| Block |
| Unblock |

Fig. 10A

REMOTE SEMICONDUCTOR MICROSCOPY

This application is a Divisional of U.S. application Ser. No. 10/118,844, filed Apr. 9, 2002 now U.S. Pat. No. 6,567,770, which is a Divisional of U.S. application Ser. No. 09/298,502, filed Apr. 23, 1999, now issued as U.S. Pat. No. 6,370,487, which is based on U.S. Provisional Patent Application No. 60/082,846 entitled "Host Based Frame Monitor for Synchronized Video Acquisition and Compression" filed Apr. 23, 1998, and U.S. Provisional Patent Application No. 60/103,669 also entitled "Host Based Frame Monitor for Synchronized Video Acquisition and Compression" filed Oct. 9, 1998, all of which are incorporated herein by reference.

TECHNICAL FIELD

This invention relates generally to the field of semiconductor devices and, more particularly, to a method and system for inspecting semiconductor wafers via remote microscopy.

COPYRIGHT NOTICE/PERMISSION

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the software and data as described below and in the drawing hereto: Copyright 1999, Micron Technology, Inc., All Rights Reserved.

BACKGROUND INFORMATION

Microscopes are used to visually analyze the structural results of semiconductor processing. Fine features of semiconductor devices, such as transistor gates having submicron dimensions, are not readily visible to the human eye. Therefore, high performance microscopes, including scanning electron microscopes (SEMs) and scanning tunneling microscopes (STMs), are used to make these features visible. Semiconductor process engineers can, therefore, view these features to more efficiently diagnose problems that exist in semiconductor processes.

Conventionally, the images produced by microscopes are present only on monitors located with the microscopes. See Lampso, B. W. and Redell, D. D. (1980), *Experience with Processes and Monitors on Mesa*, Communications of the AACM, Vol. 23, No. 2:105–117. Often, the microscopes are located in the clean room complex of a wafer fabrication facility in which semiconductor processing is performed. Thus, wafers can be inspected in the midst of semiconductor processing without their removal from the clean room complex. As a result, the wafers are less likely to be contaminated by undesired particles that exist in far greater quantity outside the clean room complex. However, because the microscopes are located within the clean room complex, process engineers must necessarily don clean room uniforms, or bunny suits, and enter the clean room complex to view the inspected wafers. This technique is particularly inefficient when the process engineers, who are not normally stationed in the clean room complex, are required to enter the clean room complex to view microscopy results.

SUMMARY OF THE INVENTION

To enhance the efficiency of wafer inspection by process engineers, the present invention provides for a method and apparatus for remote semiconductor microscopy whereby video signals are broadcast from one or more microscopes to remote viewers. In one embodiment, a live video signal is broadcast from the microscope over a network to personal computers located in the offices of process engineers. The office-based process engineers are provided real-time, or substantially real-time, views of a wafer, including peripheral views of the wafer outside cell array boundaries. The process engineer, in his office, can direct a technician, operating the microscope in the clean room complex, to display a desired cell region-of-interest with the microscope.

Further, multiple process engineers can simultaneously view the video signal from the microscope(s). As a result, the process engineers can analyze, in real-time, or substantially in real-time, the information provided by the video signals. In this way, the process engineers can more efficiently collaborate to solve process problems, or even develop new process techniques.

Therefore, it is a benefit of the present invention that it diminishes the time in which semiconductor microscopy is performed. It is a further benefit of the present invention that it permits multiple process engineers to simultaneously review microscope data in real-time, or near real-time.

BRIEF DESCRIPTION OF THE DRAWINGS

FIG. 1C is a block diagram illustrating another embodiment of a system for inspecting semiconductor wafers via remote microscopy in which video can be communicated to remote clients by a wide area network such as the Internet.

FIG. 6C illustrates one embodiment of the ProducerFrameThread subclass;

FIG. 6D illustrates one embodiment of the ConsumeFrameThread subclass;

FIG. 9A illustrates one embodiment of the Queue class;

FIG. 10A illustrates one embodiment of a BinarySemaphore class; and

DETAILED DESCRIPTION

The present invention provides a method and apparatus for remote microscopy useful to analyze semiconductor wafers. The term "wafer" used in the following description includes any structure having an exposed surface on which an integrated circuit (IC) is or may be formed. In another embodiment, the method and apparatus for remote microscopy may be used for other applications, including medical procedures. For example, during an operative procedure, and under the control of a pathologist, remote microscopy can be used to obtain diagnostic-quality images of microscopic tissue samples. The images are transmitted between geographically separated sites in real-time to permit remote consultation by other physicians. Further information about remote medical microscopy is provided in Dr. Gary J. Grimes, "Remote Microscopy for Hi Res Real-Time Interactive Pathology," *Advance Imaging*, p. 12, July 1997, hereby incorporated by reference.

Figure 1A:
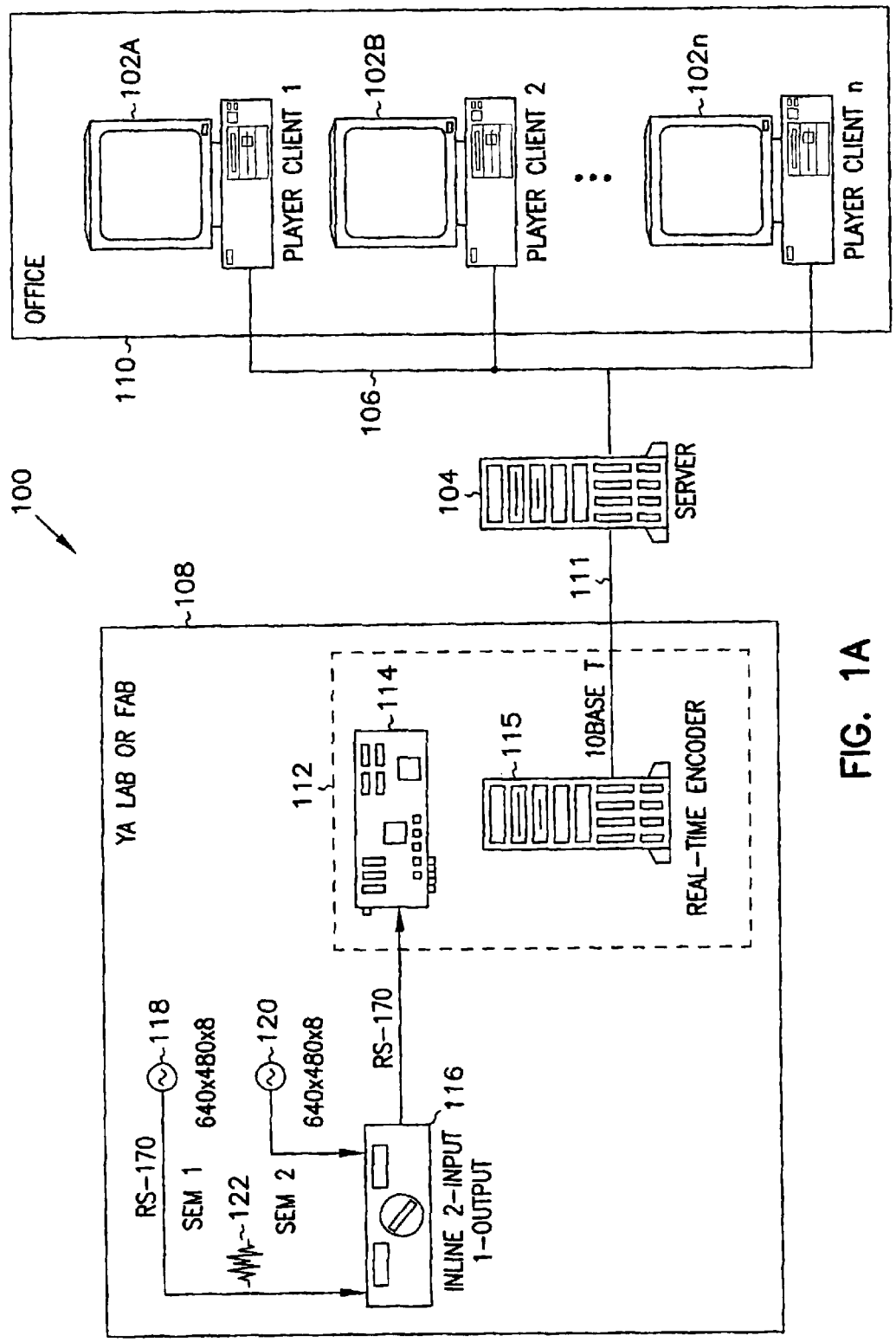
FIG. 1A is a block diagram illustrating one embodiment of a system for inspecting semiconductor wafers via remote microscopy.

FIG. 1A illustrates one embodiment of a system 100 provided by the present invention. The system 100 includes one or more client computers 102a–102n, or generally 102, coupled to a server 104 by a local area network 106. In another embodiment, the clients 102 are generally located within the offices 110 of process engineers, which are outside the clean room complex 108. However, one or more clients 102 can be placed in the clean room complex 108. The server 104 may be located within or outside the clean room complex 108.

Figure 1B:
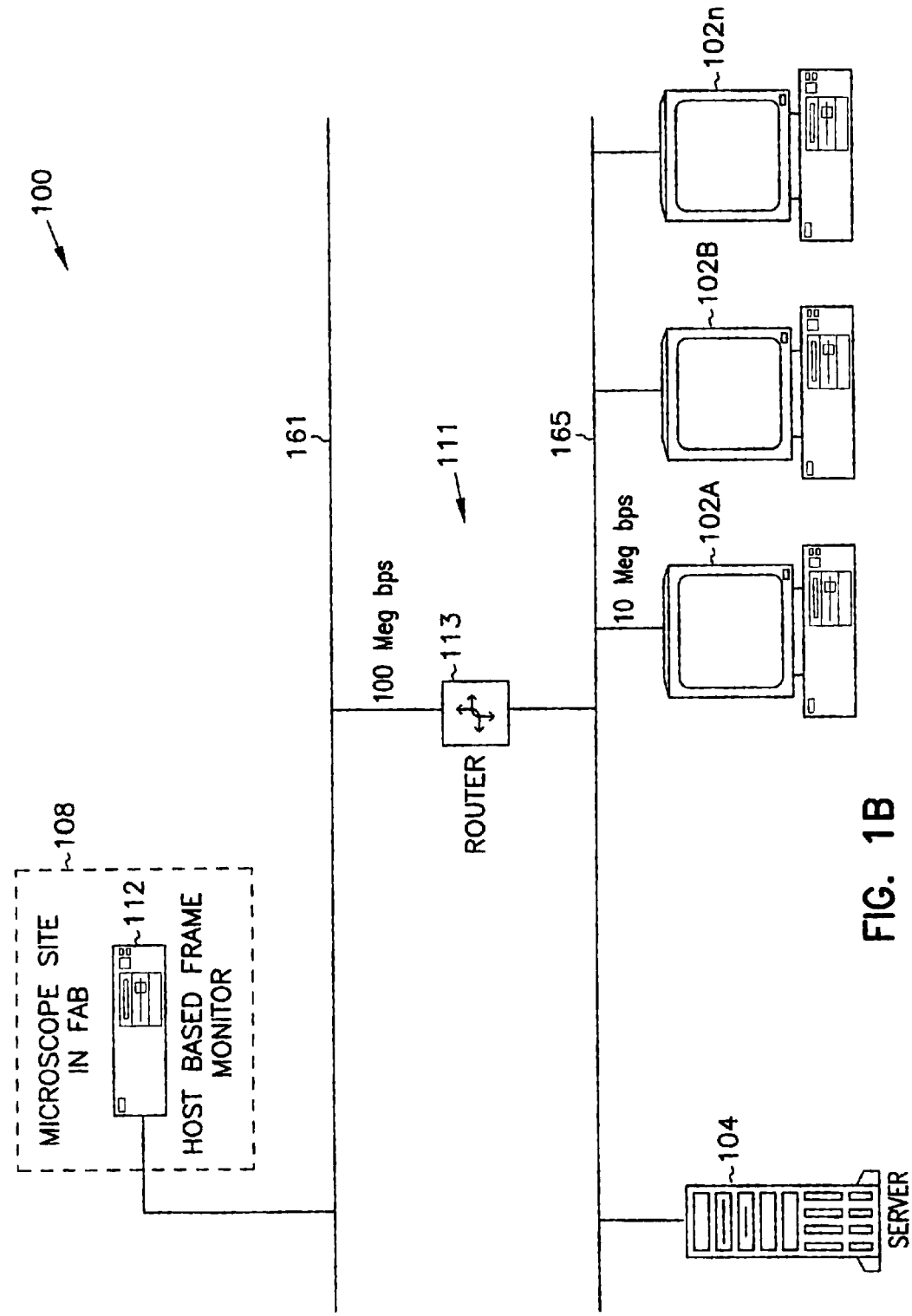
FIG. 1B is a block diagram illustrating another embodiment of a system for inspecting semiconductor wafers via remote microscopy comprising two subnetworks coupled by a router.

The server 104 is coupled to a video capture system 112 by a network 111, such as a corporate intranet. In one embodiment, illustrated in FIG. 1B, the network 111 comprises two subnetworks 161, 165 coupled by a router 113. The first subnetwork 161 couples the video capture system 112 to the router 113. The second subnetwork 165 couples the router to the server 104. The second subnetwork 165 also couples the server 104 to the clients 102. In one embodiment, the video capture system 112, server 104, and clients 102a–102n operate at 10 Megabits per second. In another embodiment, the router operates at 100 Megabits per second.

FIG. 1C illustrates another embodiment of the system 100 that utilizes a network 111 comprising the subnetworks 161, 165 coupled by a router 163, as described above. Additional clients 185a–185n, generally 185, can be coupled to the network 111 by a wide area network 187, such as the Internet, to permit unicasting of video over long distances. Further, each SEM 118, 120 is coupled to an analog multiplexer 116 through a video distribution amplifier 180, 182 having two video outputs. The output of each video distribution amplifier 180, 182, not coupled to the analog multiplexer 116, is coupled to an image still capture station 190, 192. Subsequently, the present invention will be discussed in view of the embodiment illustrated in FIG. 1A. However, such discussion may also be applicable to other embodiments.

The video capture system 112 may be located within or outside the clean room complex 108. The video capture system 112, for example a computer, includes a video capture card 114 coupled to a computer 115. In one embodiment, when the video capture card has limited, for example, one, analog video inputs, then an analog multiplexor 116 may be used to couple analog video signals from multiple microscopes 118, 120 to the video capture card 114. The analog multiplexor 116 can be manipulated directly, for example, by a microscope operator, or remotely through the system 100, for example, by a process engineer in an office 110, to select analog video signals 122, from one microscope to be broadcast to clients 102. Manipulation may be performed manually or electronically. In a further embodiment, the system 100 can control the analog multiplexor 116, for example, to automatically and sequentially select analog video signals 122 from the multiple microscopes 118, 120.

In another embodiment, when the video capture card 114 has a sufficient number of analog video inputs to uniquely couple each microscope to an analog video input, then an analog multiplexor 116 is not required in the system 100. In this embodiment, the multiplexor is part of the video capture card 114. Also, in this embodiment, the analog video inputs may be selected automatically by the system 100, or manually by the SEM operator or process engineer.

Figure 1D:
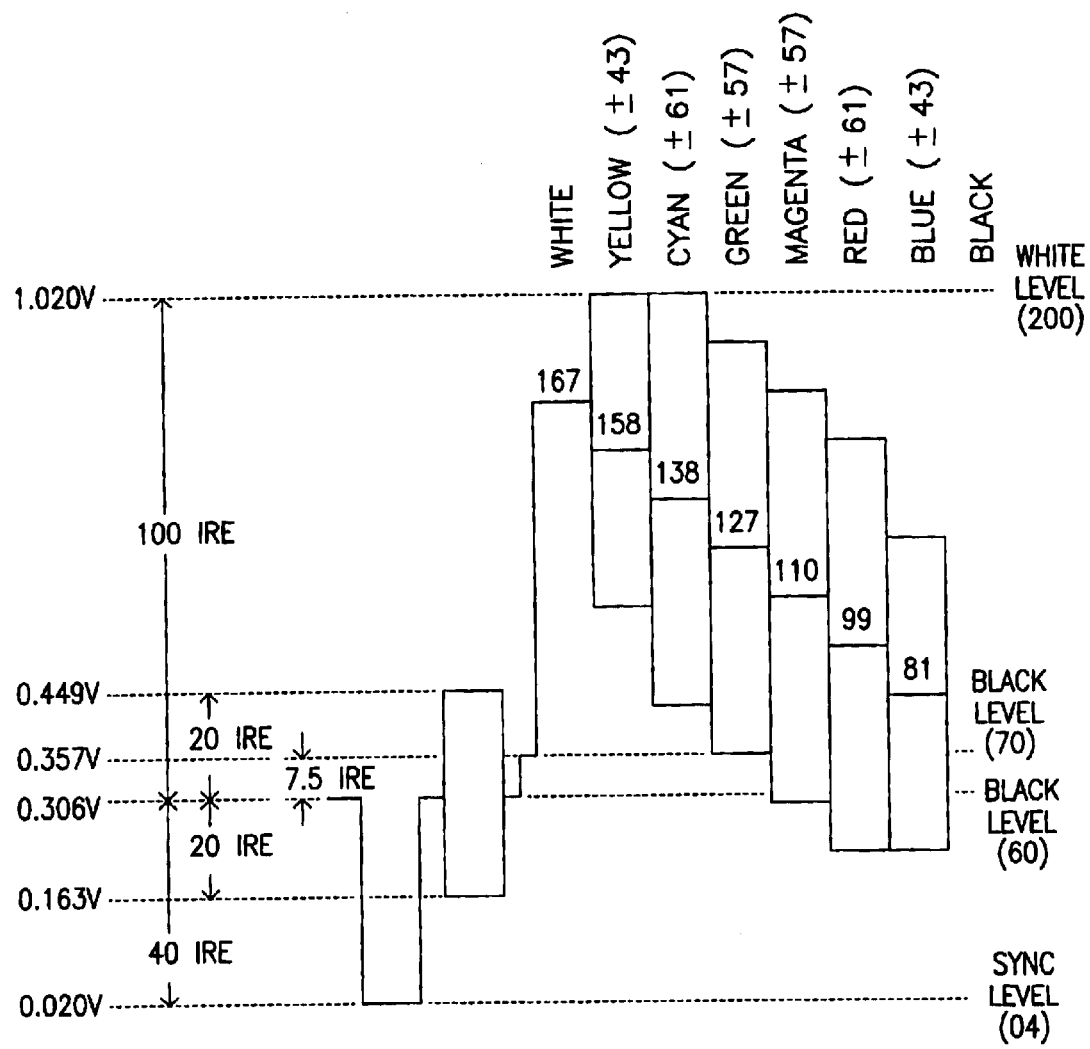
FIG. 1D illustrates one embodiment of an analog video waveform in the RS-170 format.

In yet another embodiment, the computer system operates in the following manner. The microscopes 118, 120 provide analog video signals 122. The analog video signals 122 may be in the RS-170 (without color burst) or RS-170A (with color burst) formats. One embodiment of an analog video waveform in the RS-170 format is illustrated in FIG. 1D. Alternate embodiments of such an analog video waveform 122 would include finite rise and fall times not illustrated in FIG. 1D. Analog video waveforms are further described in K. Jack, *Video Demystified: A Handbook for the Digital Engineer*, HighText, 1993, which is hereby incorporated by reference.

In one embodiment, the analog video 122 signal is coupled from the microscope to the video capture card 114 by a 75 ohm coaxial cable. If the video capture card 114 is located a substantial distance from the microscope, for example outside the clean room, a video distribution amplifier 180, 182 should be inserted between the microscope and the video capture card 114, as illustrated in FIG. 1C. In another embodiment, each frame of analog video 122 corresponds to one progressive scan of a scanning electron microscope (SEM) or scanning tunneling microscope (STM). Frames of analog video 122 from a microscope are digitized by the video capture card 114. The digitized frames of analog video 122 are provided by the video capture system 112 over the network 111 to the server 104. In one embodiment, the connection between the video capture system 112 and the server 104 uses a point-to-point transport control protocol-Internet protocol (TCP-IP). The digitized frames of analog video 122 are then stored in the server 104.

In one embodiment, still frames of video are captured, compressed and inserted into a database. Each image has a unique identifier which can be associated with a wafer or a lot of wafers. Therefore, a process engineer can select a specific frame of interest from stream content, and save a specific frame into a database.

In yet another embodiment, the digitized frames of analog video 122 are streamed over the network 106 from the server 104 to the clients 102. In a further embodiment, the streaming video format can be the Advanced Streaming Format (ASF) (Microsoft® Corporation, Redmond, Wash.), further described in a document published by Microsoft® Corporation and Real Networks™, Inc., entitled *Advanced Streaming Format (ASF) Specification*, Feb. 11, 1998, hereby incorporated by reference, and which may be found on the World Wide Web at http://www.microsoft.com/ asf/whitepr/ asfwp.htm. Frames of digitized video data 122 are streamed in the ASF format by Netshow Server software operating on the server 104. The ASF video is played on the clients 102 by Netshow Player software. Netshow software is also a product of Microsoft® Corporation (Redmond, Wash.). However, the present invention can utilize other client-server streaming software, such as Real Video by Real Networks, Inc. (Seattle, Wash.).

In yet another embodiment, the digitized frames of analog video 122 can be stored on the server 104 as a file, such as in ASF, for viewing at a later time. Thus, microscopy video can be viewed remotely at a time substantially after the digitized frames of analog video data 122 have been captured by the video capture system 112.

The video capture system 112 will now be further discussed. A video capture card 114 having a relatively high frame rate is desirable. In one embodiment, the video capture card 114 is coupled to the memory and processor of the video capture system 112 by an Industry Standard Architecture (ISA) bus. An example of a video capture card, using an ISA bus, is a Winnov Videum VO (http://www.winnov.com). However, video capture cards that operate with ISA buses have limited bandwidth. For example, ISA buses operate with 16 bits at about 4 Megabytes-per-second. Thus, for example, the video capture card has a resolution of about 640×480×8; its corresponding maximum frame buffer-to-host memory transfer rate on the ISA bus is (4 Megabytes/Second)/307,200 Bytes=13 Frames/Second.

The relatively slow frame rate of the ISA compatible video capture card limits the frame rate of the video broadcast on the local area network 106 by the server 104. Therefore, a video capture card 114 having a higher frame rate is preferably used.

Figure 2:
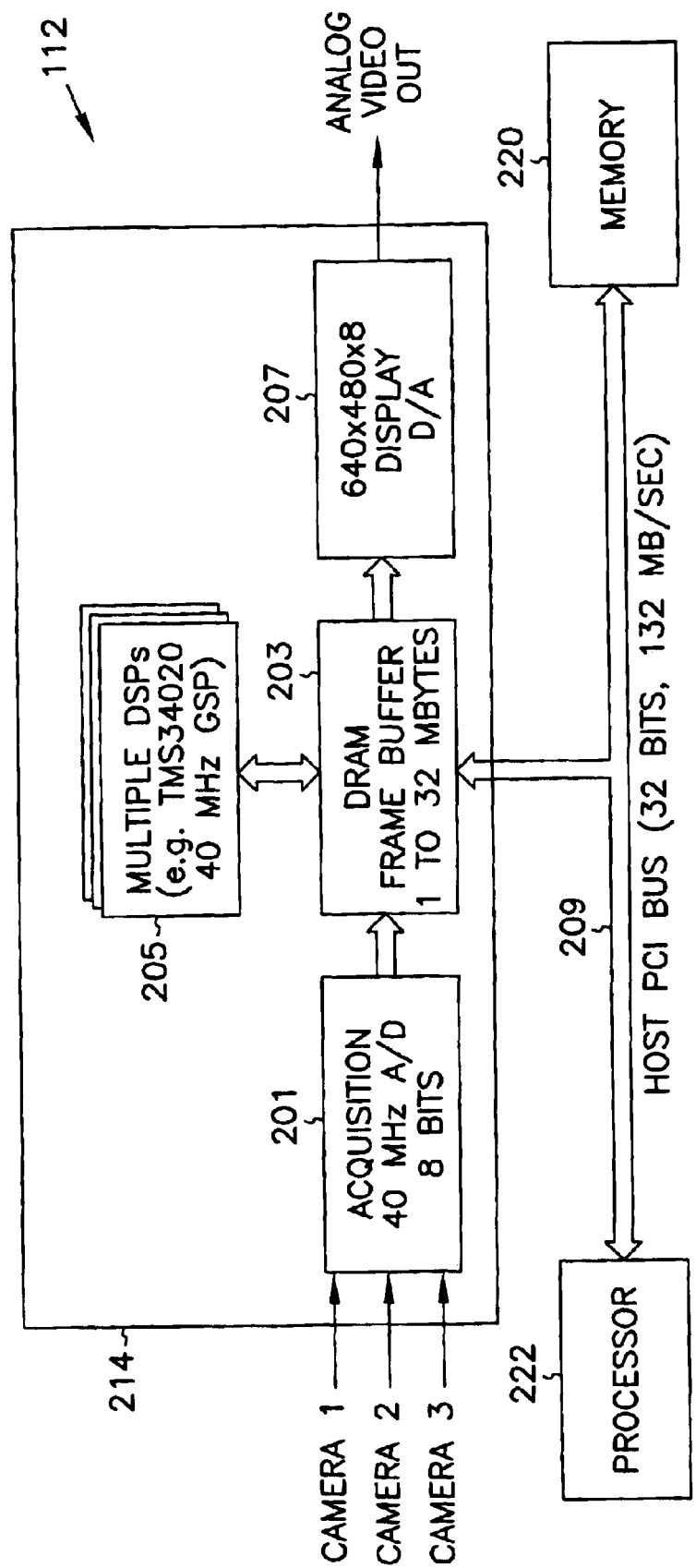
FIG. 2 illustrates one embodiment of a video capture card having a frame rate suitable for capturing and digitizing video signals representing microscopic views of semiconductor wafers.

One embodiment of a video capture card 214 having a higher frame rate is illustrated in FIG. 2. The video capture card 214 is coupled to the memory 220 and processor 222 of the video capture system 112 by a Peripheral Component Interface (PCI), or IEEE-1394, bus 209. A PCI bus compatible video capture card 214 has greater bandwidth than an ISA bus compatible video capture card.

The video capture card 214 operating with a PCI bus 209 can be implemented with either Coreco Ultra II or F/64 video capture cards. The F/64 video capture card, which originally operated with an ISA bus, includes a high speed module on a daughter board to permit operation with the PCI bus 209. The PCI bus 209 has a maximum data rate of 132 Megabytes per second. However, generally, the PCI bus 209 operates at a data rate of about 80 Megabytes per second. For 640×480×8 resolution, the PCI bus compatible video capture card 214 has a maximum frame buffer-to-host memory transfer rate of (80 Megabytes/Second)/307,200 Bytes=260 Frames/Second, which is much greater than the 13 Frames/Second rate of the ISA bus compatible video capture card. Because of its higher frame rate, the video capture card 214 operating with a PCI bus 209 can facilitate higher frame rates on a local area network 106.

The Coreco F/64 will now be further described. The video capture card 214 includes an analog to digital (A/D) converter 201. The A/D converter 201 transforms one or more analog signals, such as analog video signals, into digital signals. Thus, in one embodiment, analog video signals from a microscope can be sampled and converted to digitized video signals 122 by the A/D converter. The sampling rate and number of bits of the A/D converter 201 will vary depending upon the type of A/D converter 201 used. The A/D converter 201 is coupled to a frame buffer 203 which captures and stores digitized frames of analog video 122. However, in an alternative embodiment, digitized frames of analog video 122 can be provided from a microscope directly to the frame buffer 203. The frame buffer 203 of the Coreco F/64, for example, can store up to 32 Megabytes of data.

The Coreco F/64 includes one or more digital signal processor(s) 205, such as graphics signal and histogram processors, coupled to the frame buffer 203. The digital signal processor(s) 205 may be used to manipulate, for example, capture, filter and/or analyze, the digitized frames of analog video 122. A captured digitized frame of analog video 122 is stored in the frame buffer 203. The digitized frame can be provided efficiently from the video capture card 214 to a processor 222, such as a Pentium II processor (Intel Corporation, Santa Clara, Calif.), through the PCI bus 209 by direct memory accessing (DMA). As a result, the processor is not required to perform extra processing, such as generating addresses. Alternatively, the digitized frame can be provided to the memory 220 through the PCI bus 209.

The Coreco F/64 can perform image processing, and the inventor has used it to explore digitized video data 122 of semiconductor microscopy. Specifically, the Coreco F/64 has been used to detect motion by evaluating changes in subsequent frames.

Generally, a video signal contains inherent redundancies both spatially and in time. Spatial redundancies, or statistical dependencies among neighboring pixels, are present because naturally viewed images are generally smooth. In other words, video images comprise primarily low frequency content, in addition to structured texture regions and connected edge boundaries. Temporal redundancies, or time-related statistical dependencies, are a function of how fast or slow object scenes move, as is discussed in M. J. T. Smith and A. Docef, *A Study Guide for Digital Image Processing*, Riverdale, Ga., Scientific Publisher, 1997, hereby incorporated by reference. Digitized frames representing a semiconductor wafer generally illustrate no motion, except when a stage of the microscope is panned or optics of the microscope are adjusted. Thus, successive digitized frames of a semiconductor wafer are generally very similar to one another.

The static nature of digitized frames of semiconductor wafers can be verified by using the real-time histogram processor (Texas Instruments, Dallas, Tex.) resident on the Coreco F/64. See, *The Oculus-F/64 Frame Grabber User's Manual*, Edition 1.0, Revision 2, Coreco, Inc., p. 3–7, June 1994; http://www.coreco.com. The real-time histogram processor can analyze multiple sets of two successive (i.e., first and second) digitized frames of a semiconductor wafer. As a result, a relatively slow video frame rate of 5 frames-per-second was found to be adequate for remote microscopy of semiconductor wafers. Also, generally, the difference between means of the video information in the sets of first and second frame, approached zero. For this reason, the video data of semiconductor microscopy was found to be a suitable candidate for compression, or encoding.

Therefore, in one embodiment, the video capture system 112 includes a video encoder, such as found in the Duck True Motion Real-Time encoder-decoder (CODEC) (Duck Corporation, New York, N.Y.), which encodes, or compresses, the captured frames of digitized video, and converts them into the ASF. The HBFM can be implemented using the Component Object Model (COM) (Microsoft® Corporation, Redmond, Wash.), further described in a document published by Microsoft® Corporation entitled *The Component Object Model Specification*, version 0.9, Oct. 24, 1995. The Duck True Motion Real-Time CODEC is implemented in software, and is an In-Process Active X component that is loaded into an existing apartment when the COM client, Host Based Frame Monitor, calls CoCreateInstance.

Encoding in the present invention can be implemented in the following ways. In one embodiment, the Duck True Motion Real-Time CODEC can reside in the memory 220, volatile or non-volatile, fixed or removable, within the video capture system 112. The CODEC would then be executed by the processor 222 in the video capture system. In another embodiment, the CODEC can reside in memory on the video capture board 214, and be executed by a processor 205 on the video capture board.

The Duck True Motion Real-Time CODEC uses a wavelet compression algorithm. Currently, the Duck True Motion Real-Time CODEC can compress frames with a resolution of up to 320×240×24, and at a frame rate of 30 frames-per-second. Because the output resolution of a SEM or STM is typically only an 8 bit grey scale, the Duck True Motion Real-Time CODEC is capable of being modified to handle higher frame rates provided by a PCI bus compatible video capture board, such as the Coreco F/64.

Using compression the efficiency of the video capture system 112 can be enhanced. In one embodiment, the statistical data output of the video capture card's histogram processor, described above, can be used to sense whether a scene change occurs from a first frame to a successive second frame, as described above. If the statistical data, such as the differential mean, is less than a threshold level, the video capture system 112 will retransmit the previously broadcast encoded first frame, which can be stored in memory 220, and not expend resources (e.g. processor time) to encode and transmit the second frame.

The compressed digitized video data is provided to the server 104 over the network 111. In one embodiment, the Netshow server streams ASF video files to the clients 102 over the network 106. The video compression, described above, minimizes the network 106 bandwidth required for broadcasting, either uni- or multicasting, the remote microscopy video to clients 102. In another embodiment, the Netshow player, resident on the clients 102, also includes the Duck True Motion Real-Time CODEC, to permit decompression of the video before it is displayed on the client 102.

However, the capture or grabbing of video data, for example by the video capture card 114, and the transmission of digitized video data from a high-speed bus, such as a PCI bus, to the memory 220 or the processor 222 must be coordinated with real-time video compression. Also, as illustrated in FIG. 1, multiple video sources (e.g. SEMs) may be coupled to the video capture system 112. Therefore, the system 100 also needs a technique to permit and coordinate the capture of video signals from multiple sources.

Therefore, in another embodiment, the present invention provides a Host-Based Frame Monitor (HBFM). In one embodiment, the HBFM is a software system stored on a computer-readable medium and performed by the processor 222 of the video capture system 112. The HBFM coordinates frame capture, video data transfer along the high speed bus, and real-time encoding of video signals from multiple sources. The HBFM can also be used to integrate otherwise incompatible imaging components, such as a video capture card 114 and CODEC software. The HBFM achieves this integration by segregating and synchronizing the processing of each digitized frame of the analog video 122. For example, the HBFM ensures that write operations (such as analog-to-digital acquisition) and read operations (such as compression) are performed mutually exclusively. Also, the HBFM permits read operations to be executed in parallel to the write operations.

In one embodiment, the HBFM is implemented in software, rather than hardware, so that any number of threads may be created dynamically at run-time to service many application-specific digital image processing needs. For example, for a single frame grabber resource, which may be a video capture card 114, one thread can grab a frame of video, another thread can compress another frame of video data, while yet another thread performs edge detection analysis on another frame of video data that is being compressed. Like the CODEC, the HBFM can reside and be executed in either the video capture card 114, or the video capture system 112. In another embodiment, the HBFM can reside in memory, volatile or non-volatile, fixed or removable.

In a further embodiment, the HBFM is implemented with object-oriented software, as described in Rumbaugh et al., *Object-Oriented Modeling and Design*, Prentice Hall, 1991, hereby incorporated by reference. The Appendix illustrates an exemplary embodiment of an Host Based Frame Monitor 302 that ensures that frames of video data are grabbed and compressed, or otherwise processed, in an orderly and synchronized manner. The embodiment illustrates an object-oriented implementation including classes used within the HBFM software system and the corresponding methods that collectively provide an application programming interface for retrieving and processing digitized video. In one embodiment, a producer thread object can be instantiated to grab video frame data from a resource, such as a SEM, and store the video frame data in a frame buffer object. A consumer thread object can also be instantiated to perform real-time encoding of other video frame data in another frame buffer object.

Figure 5:
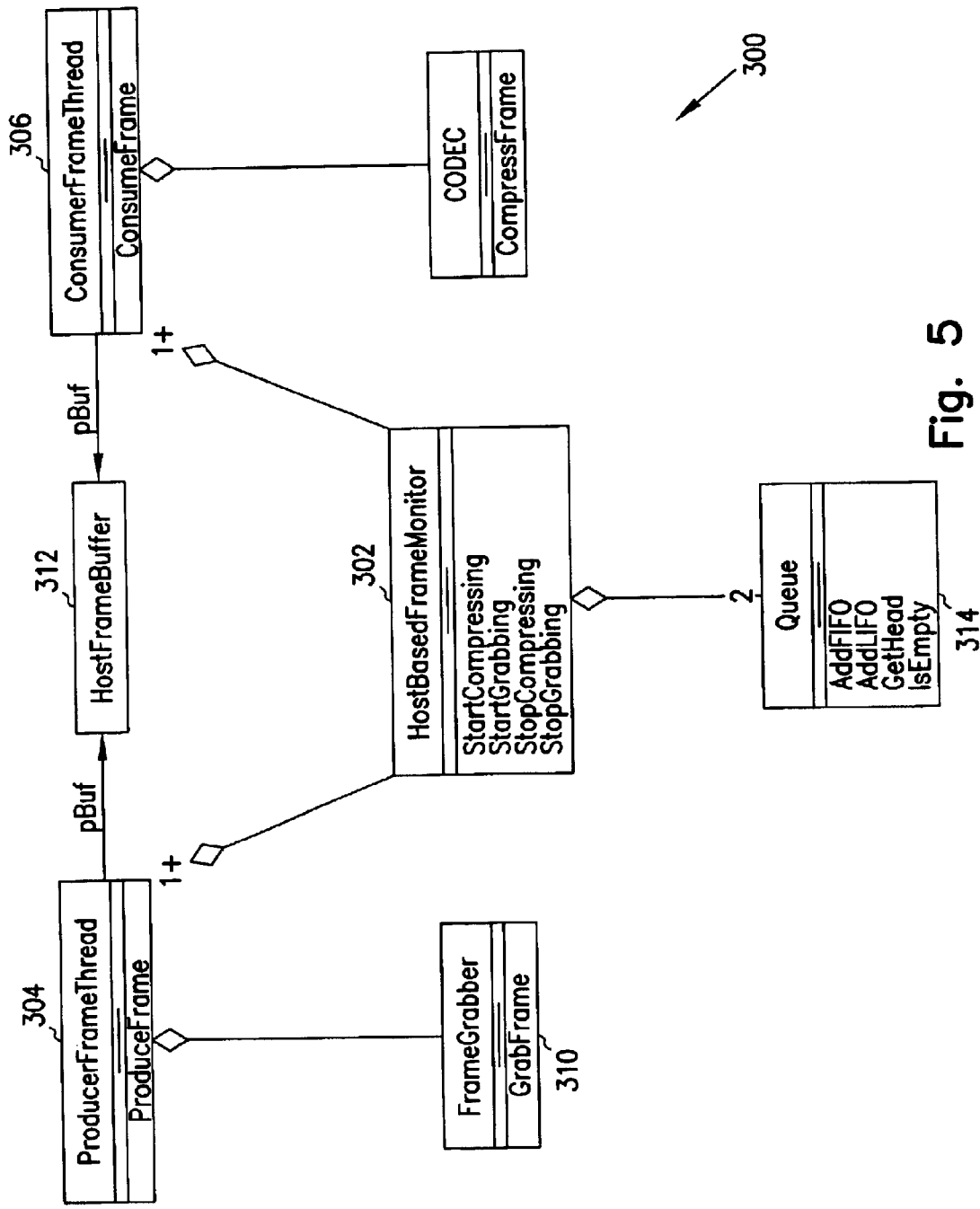
FIG. 5 illustrates one embodiment of a software system to coordinate the capture of video signals from multiple sources.

FIG. 5 illustrates one embodiment of an object-oriented software system 300 including HBFM 302. HBFM 302 can instantiate one or more producer thread objects 304 and one or more consumer thread objects 306. Each producer thread object 304 includes a ProduceFrame method to retrieve video data from frame grabber resource 310, such as video capture card 114, and store the video data in HostFrameBuffer 312. Similarly, each consumer thread object 306 includes a consumer frame method to retrieve the digitized video signal from the software frame buffer and to process the digitized video signal for communication to the remote clients 102. In this manner, the ProducerFrameThread class and the ConsumerFrameThread class present a set of application programming interfaces to HBFM 302 for retrieving, processing and communicating the digitized video signal generated by the video capture system. In another embodiment the methods are private to producer thread object 304 and consumer thread object 306 and are not available to HBFM 302.

If producer thread object 304 cannot immediately access corresponding HostFrameBuffer 312 then an identifier for producer thread object 304, such as a pointer, is placed in Queue object 314. Queue object 314 is instantiated at this time, if it does not already exist. Upon completing the grabbing of the frame, the ProduceFrame method invokes the StopGrabbing method of HBFM 302 to indicate that it has finished populating HostFrameBuffer 312 so that any ConsumerFrameThread 306 can begin operating upon the frame.

In one embodiment, the producer thread object 304 and consumer thread object 306 are executed inside a single process. Note, the HBFM 302 does not define how an analog image is digitized or how a digital image is compressed, but rather HBFM 302 ensures that frames of video data are grabbed and compressed, or otherwise manipulated, in an orderly and synchronized manner.

Figure 3:
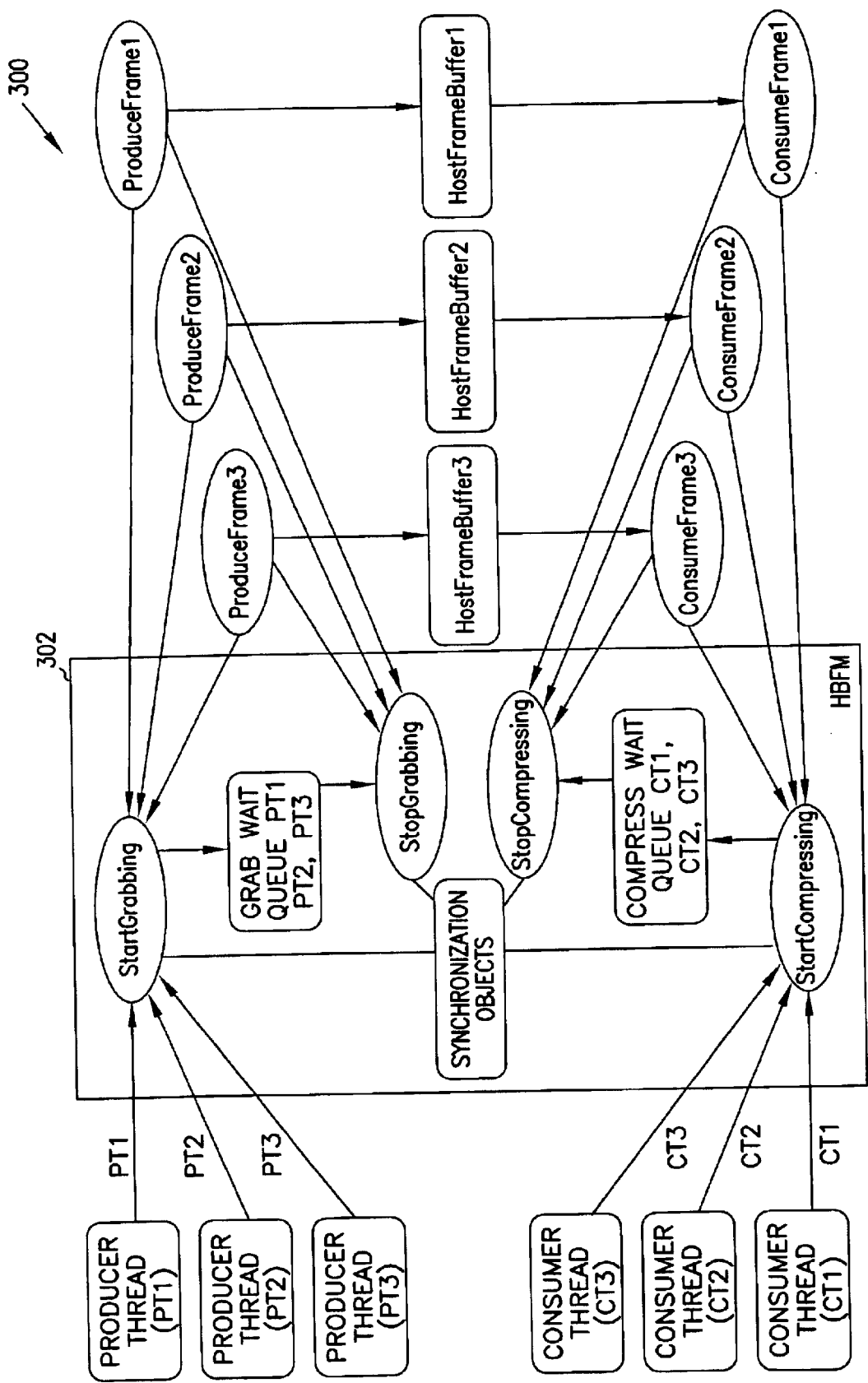
FIG. 3 further illustrates one embodiment of the software system of FIG. 5.

FIG. 3 further illustrates the object-oriented software system 300 of FIG. 5 including HBFM 302. HostFrameBuffer1, HostFrameBuffer2, and HostFrameBuffer3 are instances of HostFrameBuffer 312 of FIG. 5. ProducerThread1 (PT1), ProducerThread2 (PT2), and ProducerThread3 (PT3) are instances of ProducerFrameThread 302. Each produceFrame operation, such as produceFrame1, produceFrame2, and produceFrame3, retrieves a frame of digitized video from a corresponding HostFrameBuffer object such as HostFrameBuffer1, HostFrameBuffer2, and HostFrameBuffer3. Similarly, ConsumerThread1 (CT1), ConsumerThread2 (CT2), and ConsumerThread3 (CT3) are instances of ConsumerFrameThread 306 of FIG. 5. Each ConsumeFrame operation processes the frame of digitized video in a corresponding HostFrameBuffer object. For example, the consumeFrame operation may compress the frame of digitized video.

In one embodiment, each HBFM input signal source, such as a SEM signal, coupled to a single frame grabber resource 310, may be logically and uniquely associated with a distinct pair of producer and consumer threads as well as a corresponding HostFrameBuffer object 312. For example, referring to FIG. 3, if a frame grabber resource 310 is coupled to the outputs from three SEMs, then the most recent frame of digitized video from SEM 1 may be grabbed by the ProducerThread1 object, stored in HostFrameBuffer1 object, and compressed by the ConsumerThread1 object. The most recent frame of digitized video from SEM 2 may be grabbed by the ProducerThread2 object, stored in HostFrameBuffer2 object, and compressed by the ConsumerThread2 object. The most recent frame of digitized video from SEM 3 may be grabbed by the ProducerThread3 object, stored in HostFrameBuffer3 object, and compressed by the ConsumerThread3 object. The frames of digitized video are grabbed, stored and compressed in the manner described below.

However, for each HostFrameBuffer object HBFM 302 utilizes a single-producer/multiple-consumer locking protocol such that HBFM 302 is able to support multiple consumers for each producer. This protocol comprises two mutually exclusive states: the producer (write) state and consumer (read) state. In the write state, each HostFrameBuffer object receives a frame of digitized video from only one corresponding producer thread object at any time. In one embodiment, only one HostFrameBuffer object receives a frame of digitized video from a producer thread object at any given time. However, each HostFrameBuffer object may provide a stored frame of digitized video to one or more consumer thread objects at any given time when the HostFrameBuffer object is not receiving digitized video data from a producer thread object. This protocol has two purposes: first, multiple consumer process objects may simultaneously access a frame of digitized video in a single host frame buffer, and second, access to each frame grabber resource or video source is serialized.

In one embodiment, a single frame grabber resource may be connected to three video sources, such as cameras or SEMs. Each video source is associated with a distinct HostFrameBuffer object, and a corresponding section of the memory 220. In one embodiment, two separate processes are executed in host memory, for example, in the memory 220 of the video capture system 112. A first process may be an application or producer thread object that captures still images. A second process may be an application or a consumer thread object that performs real-time encoding.

In another embodiment, a single-process, including single producer and multiple consumer thread objects, is performed in memory 220 of the video capture system 112. The multiple consumer thread objects are permitted parallel, shared access to one HostFrameBuffer object. However, when a produceFrame method is performed by the producer thread object, only the producer thread object can update the HostFrameBuffer object with another video data frame; no consumer thread objects, or other producer thread objects, are permitted to access the HostFrameBuffer.

In one embodiment, synchronization is achieved in the following manner. A produceFrame method invokes a startGrabbing method and stopGrabbing method, respectively, before and after every frame of digitized video is grabbed. Before grabbing a new frame, a produceFrame method invokes a startGrabbing method, to make sure it can begin grabbing the new frame. If a producer thread object is not permitted to begin grabbing, and accessing its corresponding HostFrameBuffer, then the producer thread object is placed in the GrabWaitQueue object. The GrabWaitQueue object is instantiated at this time, if it does not already exist.

Upon completing the grabbing of the frame, the ProduceFrame method invokes the StopGrabbing method to indicate that it has finished populating the HostFrameBuffer object so that any consumer thread object(s) in the CompressWaitQueue can begin operating upon the frame.

A ConsumeFrame method invokes the StartCompressing method and StopCompressing method, respectively, before and after compressing a frame of digitized video, in a HostFrameBuffer object. Before compressing a frame, each consumer thread object invokes the StartCompressing method, to ensure that a producer thread object is not currently writing to the HostFrameBuffer object. If a producer thread object is currently writing to the HostFrameBuffer object, the consumer thread object is not permitted access to the HostFrameBuffer, and is placed in the CompressWaitQueue object. If not already existing, the CompressWaitQueue object is instantiated at this time.

After compressing the frame of digitized video in a HostFrameBuffer object, the ConsumeFrame method invokes the StopCompressing method to signal that it has finished compression so that a producer thread object seeking to use the HostFrameBuffer can be activated.

Figure 4:
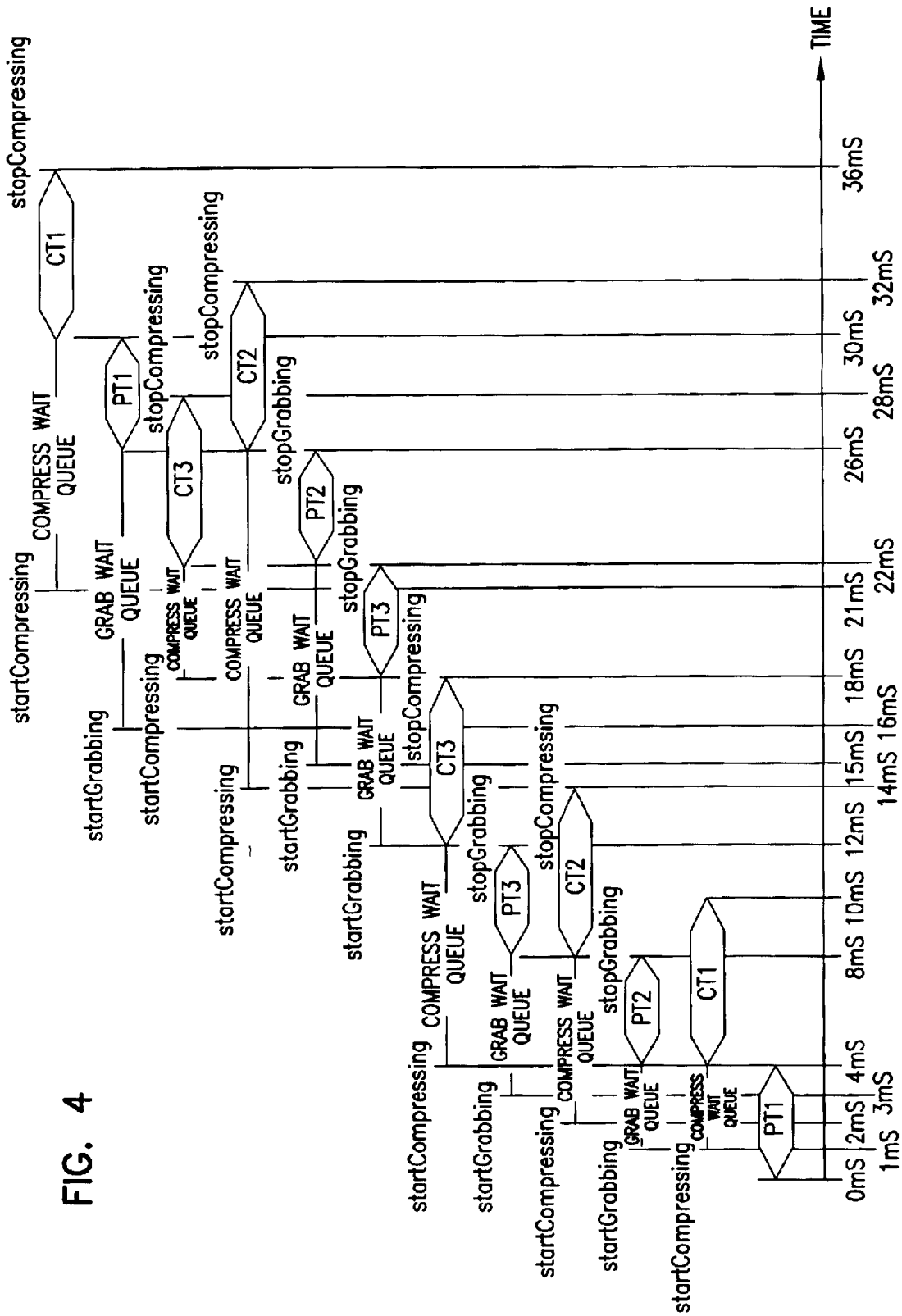
FIG. 4 illustrates an exemplary timing diagram for the software system of FIGS. 3 and 5 when a single frame-grabbing resource is utilized.

FIG. 4 illustrates an exemplary timing diagram for software system 300 including HBFM 302 when a single frame-grabbing resource is utilized. Initially, at time zero, PT1 invokes the Framegrabbers GrabFrame operation to begin to populate the Hostframe buffer object. At 1 millisecond in time, CT1 is placed on the CompressWaitQueue object because PT1 is not finished grabbing the frame.

Also at 1 millisecond, PT2 is placed in the GrabWaitQueue object because PT1 is not finished grabbing the frame. Only one producer thread object can access the frame grabber resource at a time. At 2 milliseconds, CT2 is placed in the CompressWaitQueue object because PT2 has not yet populated the HostFrameBuffer2 object. At 3 milliseconds, PT3 is placed in the GrabWaitQueue object because PT1 is still not finished grabbing the frame. Finally, at 4 milliseconds, PT1 finishes its frame grab and CT1 is permitted to access the frame stored in HostFrameBuffer1 object so that it can invoke the CODEC's CompressFrame operation. Thus, at 4 milliseconds, PT2 is permitted to proceed to write a frame to HostFrameBuffer2 object. Also, at 4 milliseconds, CT3 is placed in the CompressWaitQueue object because PT3 has not begun grabbing a frame.

For all producer threads PT1–PT3, the task of grabbing a frame is delegated to the FrameGrabber object; specifically its GrabFrame operation. For all consumer threads CT1–CT3, the task of compression (also called encoding) is delegated to the CODEC; specifically its CompressFrame operation. At 8 milliseconds, while CT1 delegates compression of the frame stored in HostFrameBuffer1 object to the CODEC object, PT2 finishes writing a frame. Thus, after 8 milliseconds, PT3 is removed from the GrabWaitQueue object, and proceeds to write a frame to HostFrameBuffer3 object. Further, CT2 is removed from the CompressWaitQueue object, and begins compressing the frame in HostFrameBuffer1 object.

At 10 milliseconds, CT1 finishes compressing the frame stored in HostFrameBuffer2 object. At 12 milliseconds, PT3 finishes writing the frame to HostFrameBuffer3 object. Thus, at this time, CT3 is removed from the CompressWaitQueue object, and begins compressing the frame stored in HostFrameBuffer3 object. Also, at 12 milliseconds, PT3 wants to produce a new frame, but cannot because CT3 is accessing the frame stored in HostFrameBuffer3 object. Therefore, PT3 is placed in the GrabWaitQueue object.

At 14 milliseconds, CT2 is placed in the Compress Wait Queue object because PT2 has not begun grabbing. At 15 milliseconds, PT2 also wants to produce a new frame, but cannot because PT3 is in the Grab Wait Queue object.

Therefore, PT2 is also placed in the Grab Wait Queue object after PT3. At 16 milliseconds, PT1 also wants to produce a new frame, but cannot because PT3 and PT2 are in the Grab Wait Queue. Therefore, PT1 is also placed in the Grab Wait Queue object after PT3 and PT2.

Once CT3 finishes compressing the frame stored in HostFrameBuffer3 object at 18 milliseconds, PT3 begins to write another frame to HostFrameBuffer3 object. Also at 18 milliseconds CT3 again wants to compress another frame stored in HostFrameBuffer3 object. Because PT3 has not completed writing another frame, CT3 is placed in the Compress Wait Queue object.

At 21 milliseconds, CT1 wants to compress another frame in HostFrameBuffer1 object. However, because PT1 has neither begun nor completed its writing of another frame to HostFrameBuffer1 object, CT1 is placed in the Compress Wait Queue object.

PT3 completes writing a frame at 22 milliseconds. Then, at 22 milliseconds, CT3 begins compressing this frame stored in HostFrameBuffer3 object. Also at 22 milliseconds, PT2 is removed from the GrabWaitQueue object, and proceeds to write another frame to HostFrameBuffer2 object.

At 26 milliseconds, PT2 finishes writing the frame to HostFrameBuffer2 object, and CT2 is permitted to compress the frame stored in HostFrameBuffer2 object. Also at 26 milliseconds, PT1 is moved off the GrabWaitQueue object, and begins writing a frame to HostFrameBuffer1 object. At 28 milliseconds, CT3 completes compressing the frame stored in HostFrameBuffer3 object.

PT1 stops grabbing the corresponding frame at 30 milliseconds. Thus, at 30 milliseconds, CT1 is taken from the CompressWaitQueue object, and begins compressing the frame stored in HostFrameBuffer1 object. CT2 and CT1 complete their compressions respectively at 32 and 36 milliseconds.

Conclusion

Various embodiment are described for remote semiconductor microscopy whereby video signals are broadcast from one or more microscopes to remote viewers. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. For example, those of ordinary skill within the art will appreciate that in one embodiment, a live video signal is broadcast from the microscope over a network to client computers located in the offices of process engineers. In another embodiment the process engineers can selectively view still images retrieved from a database. The client computers may receive the video signals via a local network or even a wide area network such as the Internet. In addition, the method and apparatus for remote microscopy may be used for other applications, including medical procedures.

Appendix

This Appendix illustrates an exemplary embodiment of an Host Based Frame Monitor (HBFM) that ensures that frames of video data are grabbed and compressed, or otherwise processed, in an orderly and synchronized manner. The embodiment illustrates an object-oriented implementation including classes used within the HBFM software system and the corresponding methods that collectively provide an application programming interface for retrieving and processing digitized video.

Class Name: HostBasedFrameMonitor

Synchronizes production and consumption operations required for grabbing and compressing digital image frames.

Figure 8A:
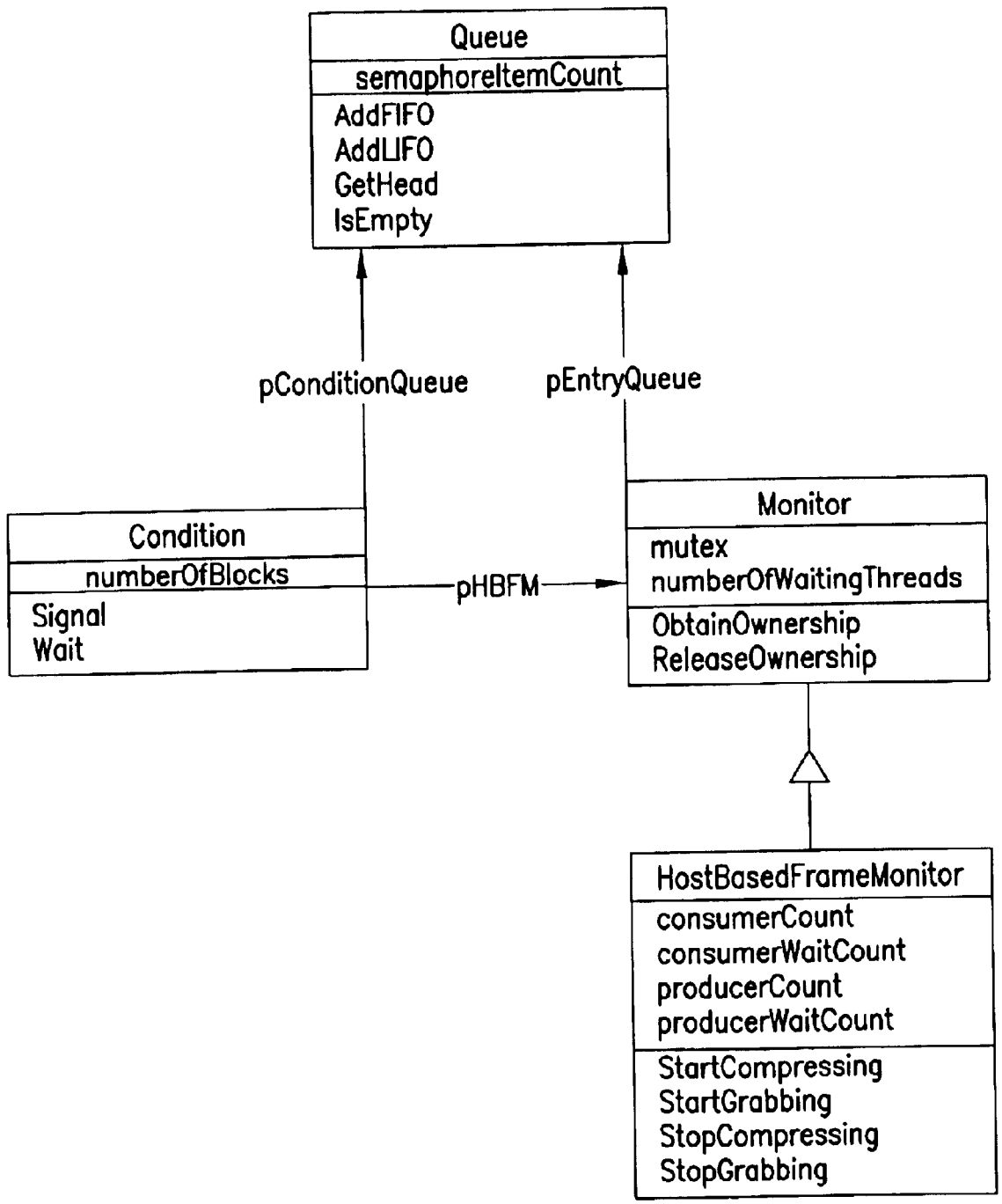
FIG. 8A illustrates one implementation of the HostBasedFrameMonitor.

Associations:

The HostBasedFrameMonitor is a specialized kind of Monitor. [Refer to FIG. 8A.]

Figure 6A:
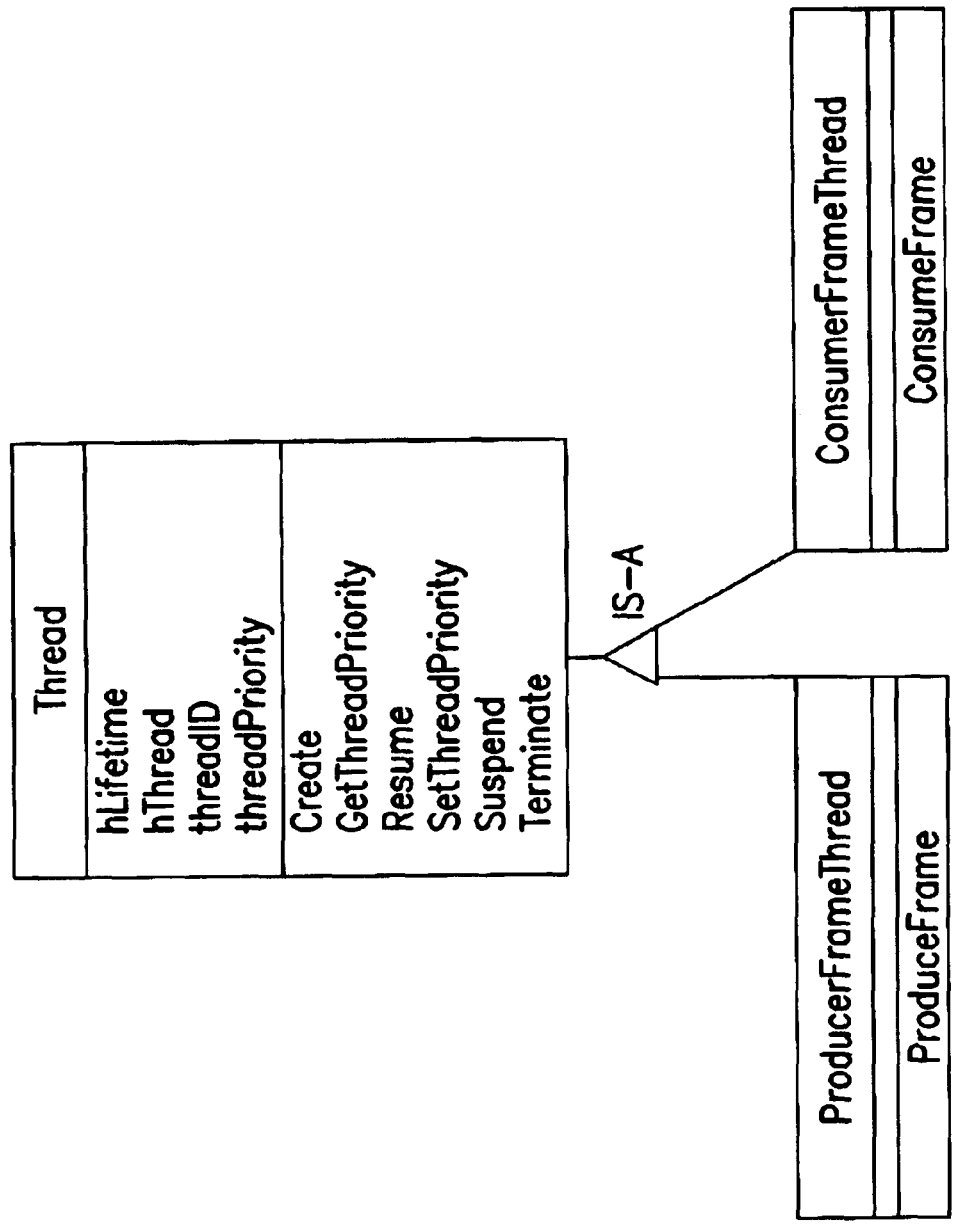
FIG. 6A illustrates one embodiment of a Thread class and related subclasses ProducerFrameThread and ConsumerFrameThread.

One HostBasedFrameMonitor is part of one or more ProducerFrameThread(s) and the same HostBasedFrameMonitor is part of one or more ConsumerFrameThread(s). [Refer to FIGS. 5 and 6A.]

The HostBaseFrameMonitor is made up of two Queue(s). One Queue instance is the GrabWaitQueue, pGrabWaitQueue, and the other Queue is the CompressWaitQueue, pCompressWaitQueue. [Refer to FIGS. 5 and 9A.]

Figure 6B:
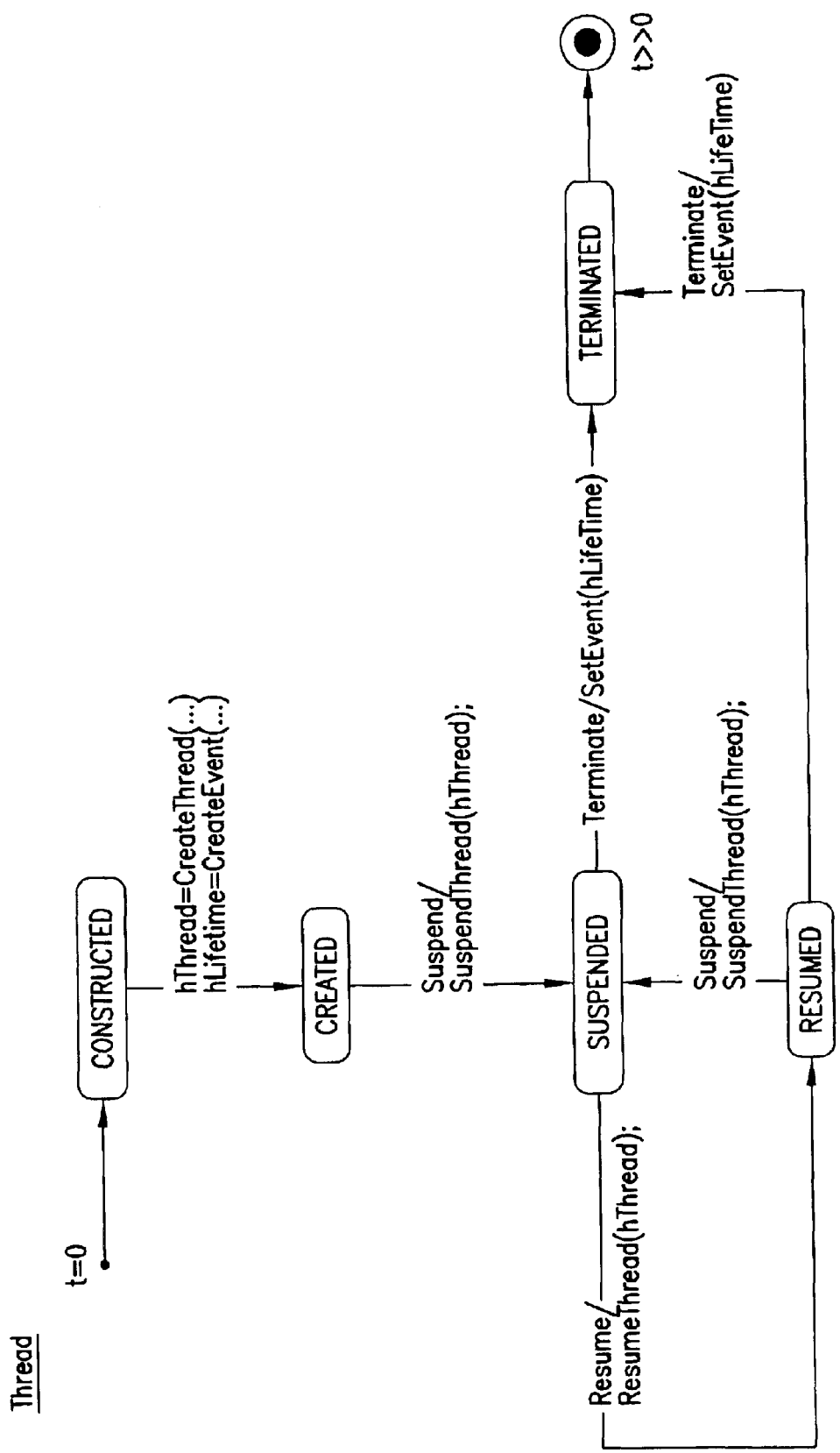
FIG. 6B illustrates a state diagram for one embodiment of the Thread class.
Figure 6E:
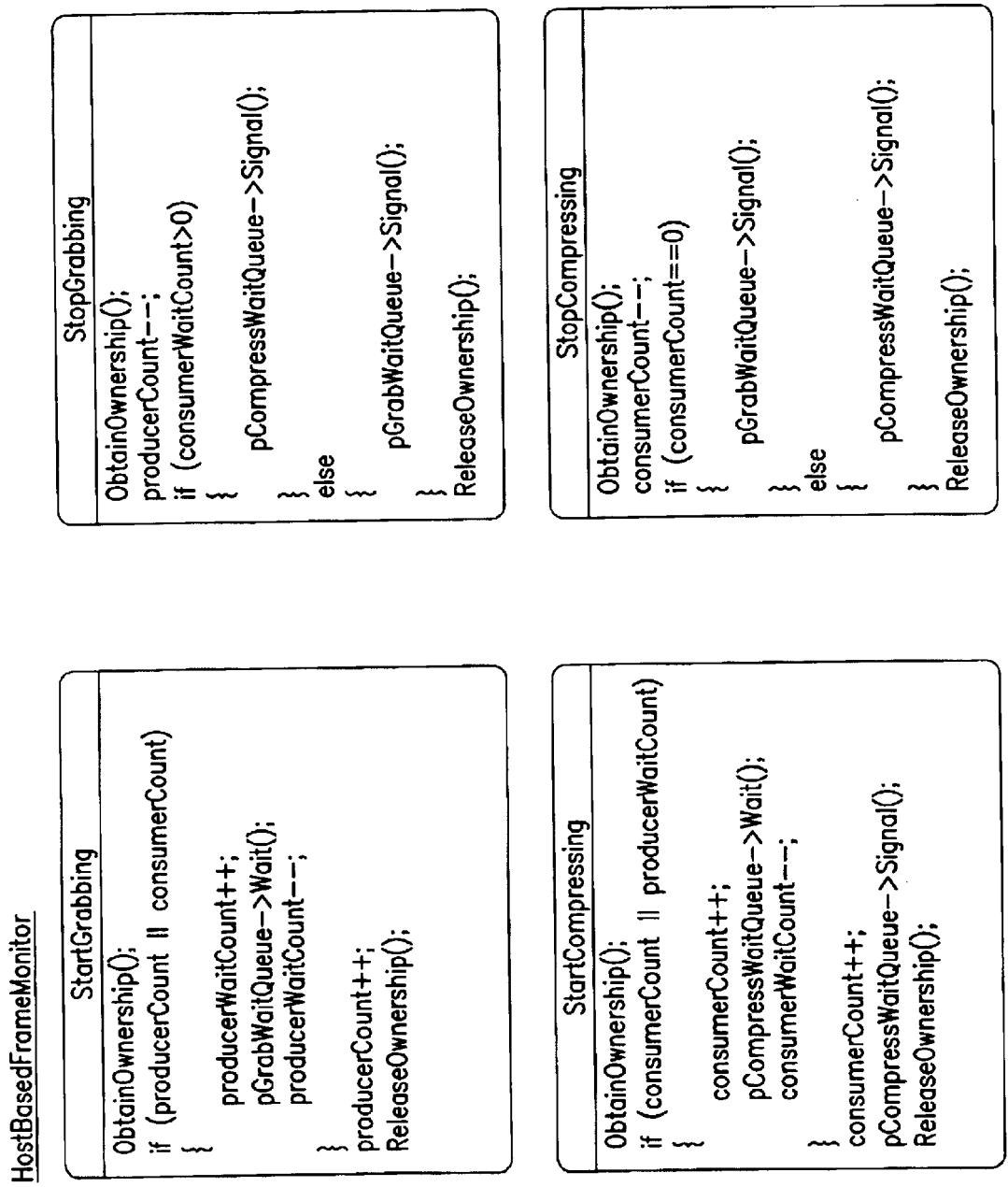
FIG. 6E illustrates one embodiment of the HostBasedFrameMonitor subclass.

Attributes:

consumerCount—The number of ConsumerFrameThreads who are accessing the HostFrameBuffer.

consumerWaitCount—The number of ConsumerFrameThread who are waiting to enter the HostBasedFrameMonitor in order to access the HostFrameBuffer.

producerCount—The number of ProducerFrameThreads who are accessing the HostFrameBuffer.

producerWaitCount—The number of ProducerFrameThread(s) who are waiting to enter the HostBasedFrameMonitor in order to access the HostFrameBuffer. [Refer to FIG. 6E]

Operations:

StartCompressing—If there are no other ProducerFrameThread(s) or ConsumerFrameThread(s) accessing or waiting to access the HostFrameBuffer, then the ConsumerFrameThread is allowed to proceed by invoking the CODEC's compressFrame operation. Otherwise, the ConsumerFrameThread is placed on the CompressWaitQueue.

StopCompressing—If there are no other ConsumerFrameThread(s) waiting to access the HostFrameBuffer, then the one and only ProducerFrameThread is signaled to proceed. Otherwise, the CompressThread who has waited the longest on the CompressWaitQueue is signaled to consume.

StartGrabbing—If there are no other ConsumerFrameThread(s) accessing or waiting to access the HostFrameBuffer resource, then the ProducerFrameThread is allowed to proceed by invoking the FrameGrabber's grabFrame operation. Otherwise, the ProducerFrameThread is placed on the GrabWaitQueue.

StopGrabbing—If there are any ConsumerFrameThread(s) waiting to access the HostFrameBuffer, then the oldest ConsumerFrameThread who has waited the longest in CompressWaitQueue is signaled to start consume. Otherwise allow the oldest ProducerFrameThread on the Grab WaitQueue [Refer to FIG. 6E]

Class Name: Thread

The Thread class provides control operations dedicated to deterministic state dynamics of an operating system resource known as a thread. Refer to FIG. 6A.

Attributes:
hLifetime—An auxiliary handle to an operating system event object used to assist in thread creation and thread termination. This event is a manual-reset type of event provided by the operating system. Internal to this class the event can be OWNED at creation time. When terminate operation is invoked, the event becomes AVAILABLE.

hThread—The handle to the actual operating system thread object instance provided by the operating system.

threadID—The identifier provided by the operating system which uniquely identifies a thread instance resident in the process.

threadPriority—Specifies the priority value for the thread.

State:
A synchronization event object with manual-reset behavior is used to control Thread creation and Thread termination. Upon successful Thread creation the state is CREATED. Upon successful Thread termination the state is TERMINATED. During the Thread's lifetime, two additional states are used: SUSPEND and RESUME. [Refer to FIG. 6B]

Operations:
Create—Bring a new thread to life. Upon successful creation, a transition to the SUSPENDED state, the threadID, threadHandle, and lifetimeHandle are each initialized.

GetThreadPriority—Allows the client to access the threadPriority attribute.

Resume—The thread is moved, per its threadID, from the SUSPENDED state to the RESUMED state.

Suspend—The thread is moved, per its threadID, from the CREATED state or RESUMED state to the SUSPENDED state.

Terminate—The thread is moved, per its threadID, from the SUSPENDED state or RESUMED state to the TERMINATED state.

SetThreadPriority—Allows the client to change the threadPriority attribute.

class Name: ProducerFrameThread

The producerFrameThread is dedicated to the production of raster frames.

Associations
The ProducerFrameThread subclass is a specialized kind of Thread class.

A ProducerFrameThread is related to only one HostFrameBuffer, pBuf.

A ProducerFrameThread is related to only one FrameGrabber, pFrameGrabber.

A ProducerFrameThread is made up of only one HostBasedFrameMonitor, pHBFM. [Refer to FIG. 5]

Operations:
ProduceFrame—When not blocked by the Monitor. the ProduceFrame operation continuously populates the HostFrameBuffer with raster data. This raster data originates from the FrameGrabber. [Refer to FIG. 6C]

Class Name: ConsumerFrameThread

The ConsumerFrameThread is dedicated to consuming the contents of the HostFrameBuffer.

Associations:
The ConsumerFrameThread is a specialized kind of Thread class.

A ConsumerFrameThread is related to only one HostFrameBuffer, pBuf.

A ConsumerFrameThread is related to only one CODEC, pCODEC.

A ConsumerFrameThread is made up of only one HostBasedFrameMonitor, pHBFM. [Refer to FIG. 5]

Operations:
ConsumeFrame—When not blocked by the Monitor, the ConsumeFrame operation continuously delegate the task of encoding (compressing) the contents of the HostFrameBuffer to the CODEC. [Refer to FIGS. 5 and 6D]

Class Name: BLOb

Figure 7:
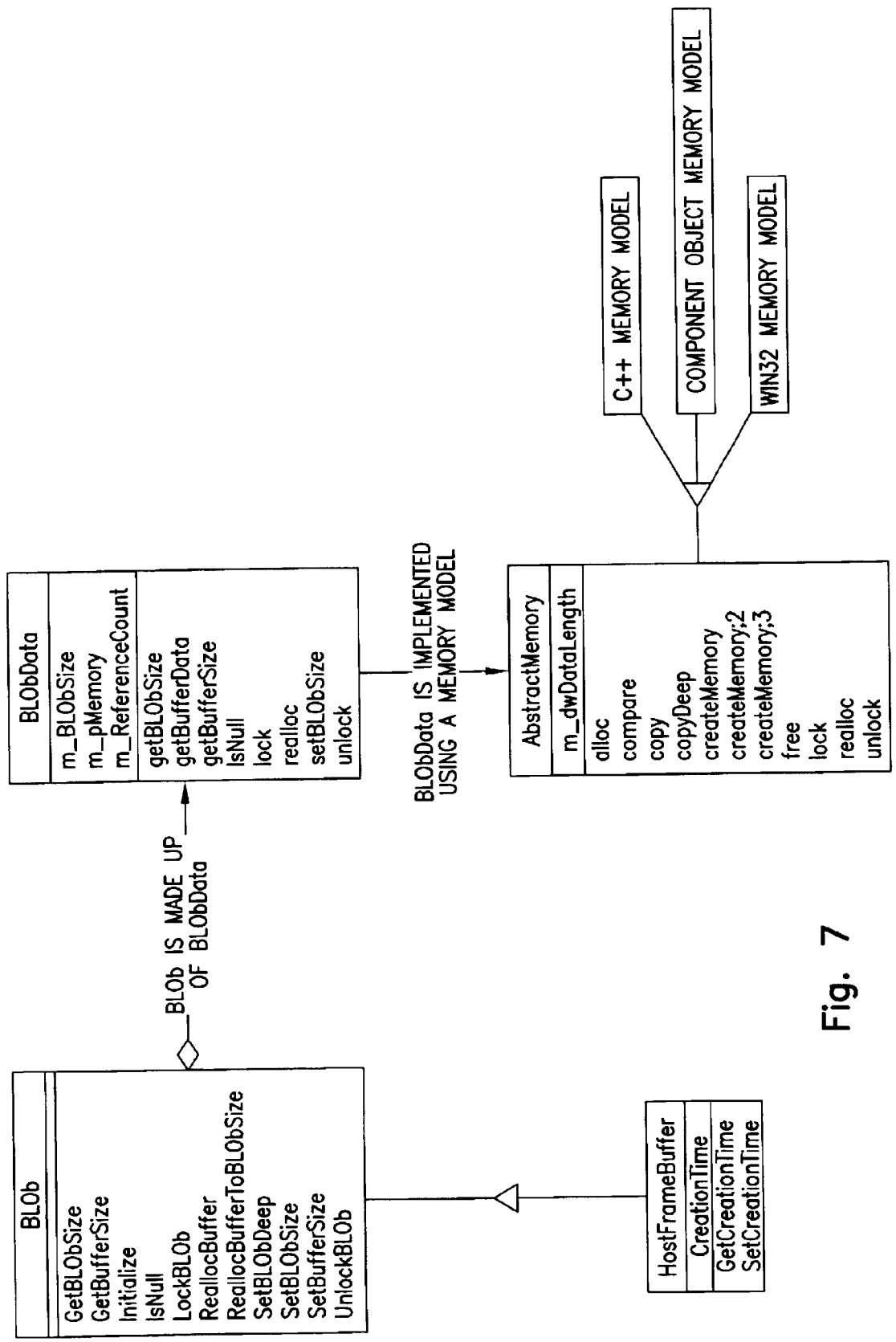
FIG. 7 illustrates one implementation of the HostFrameBuffer.

Binary data is the heart of the raster frame structure and it was therefor appropriate to abstract this key entity into a class called Binary Long Object (BLOb). The class BLOb enables the client to access large pixel data. For example, a BLOb object can be used to hold an uncompressed raster frame prior to being compressed by a CODEC or it can be used to transfer a raster from a FrameGrabber. The BLOb class contains a pointer to the class BLObData. To relieve the client from heap memory management, reference counting is employed. For clients who require direct memory access to the raster frame, the Lock and Unlock operations are provided. During a raster frame lock, reference counting is not incremented and it is the responsibility of the client to control any outstanding shallow references to the raster frame. When the client is finished with the raster frame, the client must call the Unlock operation to re-invoke reference counting. [Refer to FIG. 7]

Assertion:
BLObSize<=bufferSize

Operations:
GetBLOBSize—Return the size of the raster contained inside the buffer.

GetBufferSize—Returns the size of the allocated buffer.

Initialize—Deallocate memory associated with the raster if there is any.

IsNull—Determine if the BLOb contains valid raster data.

LockBuffer—Turn the reference counting off and obtain access to the start address of the raster frame.

ReallocBuffer—Change the size of the buffer to accommodate raster frame growth.

ReallocBufferToBLObSize—Adjust the size of the allocated buffer to match the size of the contained raster frame.

SetBLObDeep—Set the contents of the BLOb with new raster frame by performing a deep memory copy from client's source raster frame.

SetBLObSize—For all the allocated buffer memory, set the length of the contained raster frame.

SetBufferSize—Set the size of the Buffer.

UnlockBLOb—Turn reference counting on.

Class Name: HostFrameBuffer

The HostFrameBuffer is derived from the superclass Binary Long Object (BLOb). The HostFrameBuffer contains the frame raster data produced by the ProducerThread. Once the HostFrameBuffer is populated and time stamped the ConsumerThread accesses this frame faster data for encoding. [Refer to FIG. 7]

Attributes:

CreationTime—Represents an absolute time and date of when the HostFrameBuffer was populatated with new raster frame data. The creationTime incorporates the ANSI time_ data type and its associated run-time functions. creationTime values are based on coordinated universal time (UTC), which is equivalent to Greenwich mean time (GMT). The local time zone is controlled by an internal environment variable provided by the operating system.

Operations:

SetCreationTime—write-only access to set the time when the BLOb was created.

GetCreationTime—read-only access to when the BLOb was created.

Class Name: Monitor

The monitor class provides protection and synchronization of a shared resource.

Association:

pEntryQueue—The Monitor is associated with one Queue. This Queue is responsible for ordering Threads who have requested to enter the Monitor. These new Threads are placed on the entry queue if the Monitor is already Locked. [Refer to FIG. 8A]

Attributes:

hMutex—The mutual exclusion synchronization object which is provided by the operating system and is used to permit only one thread at a time from entering the Monitor.

numberOfWaitingThreads—The number of Thread(s) suspended on the associated pEntryQueue who desire Monitor ownership.

State:

The hMutex synchronization object yields two states: LOCKED and UNLOCKED.

When the Monitor is in a LOCKED state, a single Thread resides in the Monitor.

When the Monitor is in an UNLOCKED state, the next Thread in the entry Queue is permitted to transition to the LOCKED state.

Figures 2, 8B:
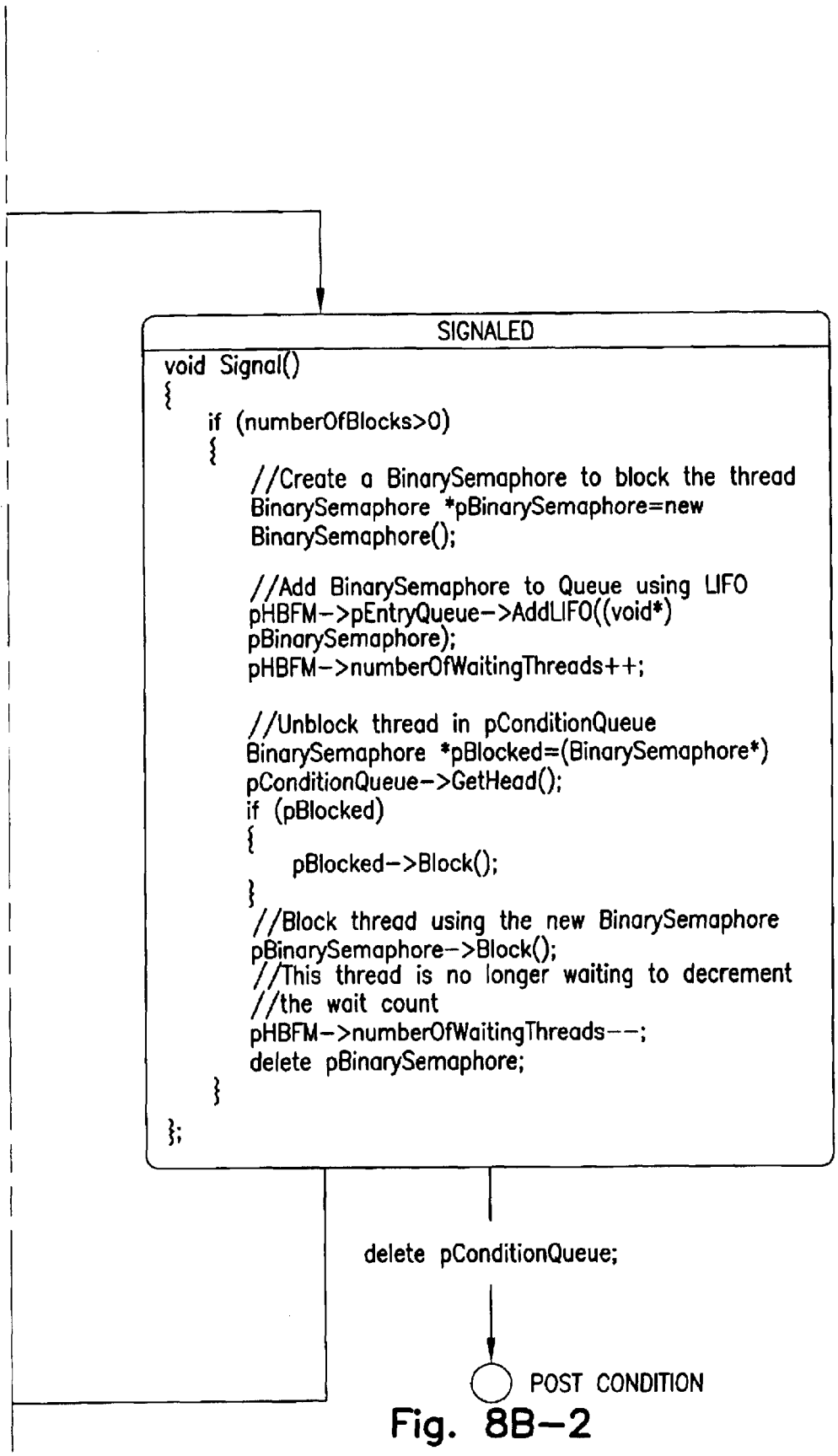
FIG. 8B illustrates an exemplary state diagram for the Condition class.
Figure 8C:
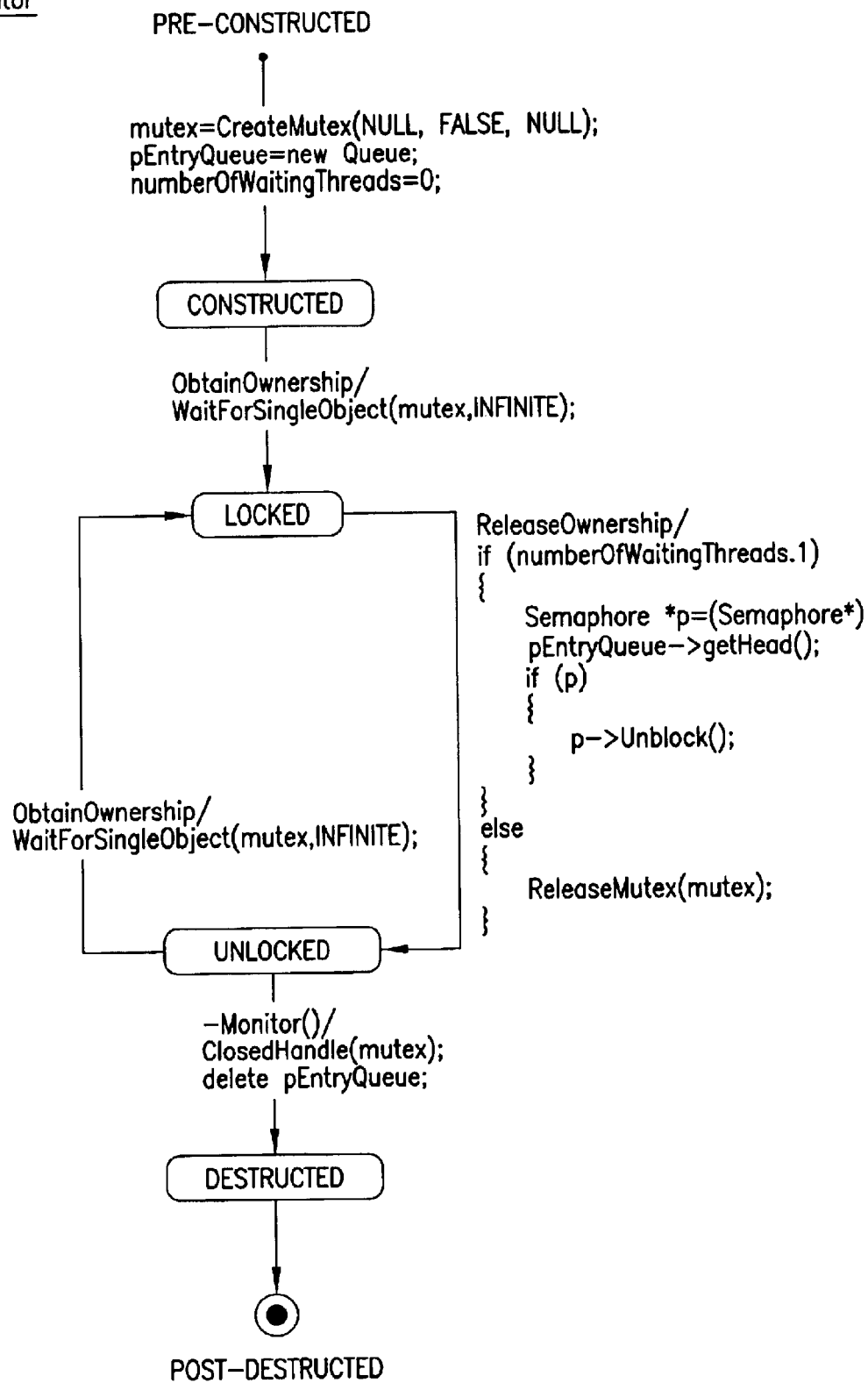
FIG. 8C illustrates an exemplary state diagram for the Monitor class.

The CONSTRUCTED AND DESTRUCTED states ensure correct initialization and de-initialization of the Monitor object. [Refer to FIG. 8C]

Operations:

ObtainOwnership—A Thread calls this operation to obtain exclusive ownership of the Monitor.

ReleaseOwnership—A Thread calls this operation to releases its ownership of the Monitor for the next stacked Thread on the entry queue.

Class Name: Condition

The Condition class is responsible for creating BinarySemaphore(s) which make Threads wait their turn in order to access the HostFrameBuffer object.

Associations

The Condition is associate with one HostBasedMonitor, pHBFM.

The Condition is associated with one Queue, pConditionQueue. [Refer to FIG. 8A]

State:

The Condition object has two states: SIGNALED and WAITING [Refer to FIG. 8B]

Attributes:

numberOfBlocks—The number of blocked threads waiting on a BinarySemaphore instance.

Operations:

Signal—Take thread off Queue and allow it to access to the Monitor.

Wait—Make thread wait its turn on Queue.

Class Name: Queue

Each SemaphoreItem refers to one SemaphoreItem.

The Queue supports two common behaviors:

First In First Out (FIFO)

Last In First Out (LIFO)

Associations:

Logically, the Queue class contains zero or more SemaphoreItem objects. However, to implement the Queue, only the addresses of the first and last SemaphoreItem are required.

The pointer pHead is the address of the first SemaphoreItem in the Queue.

Figure 9B:
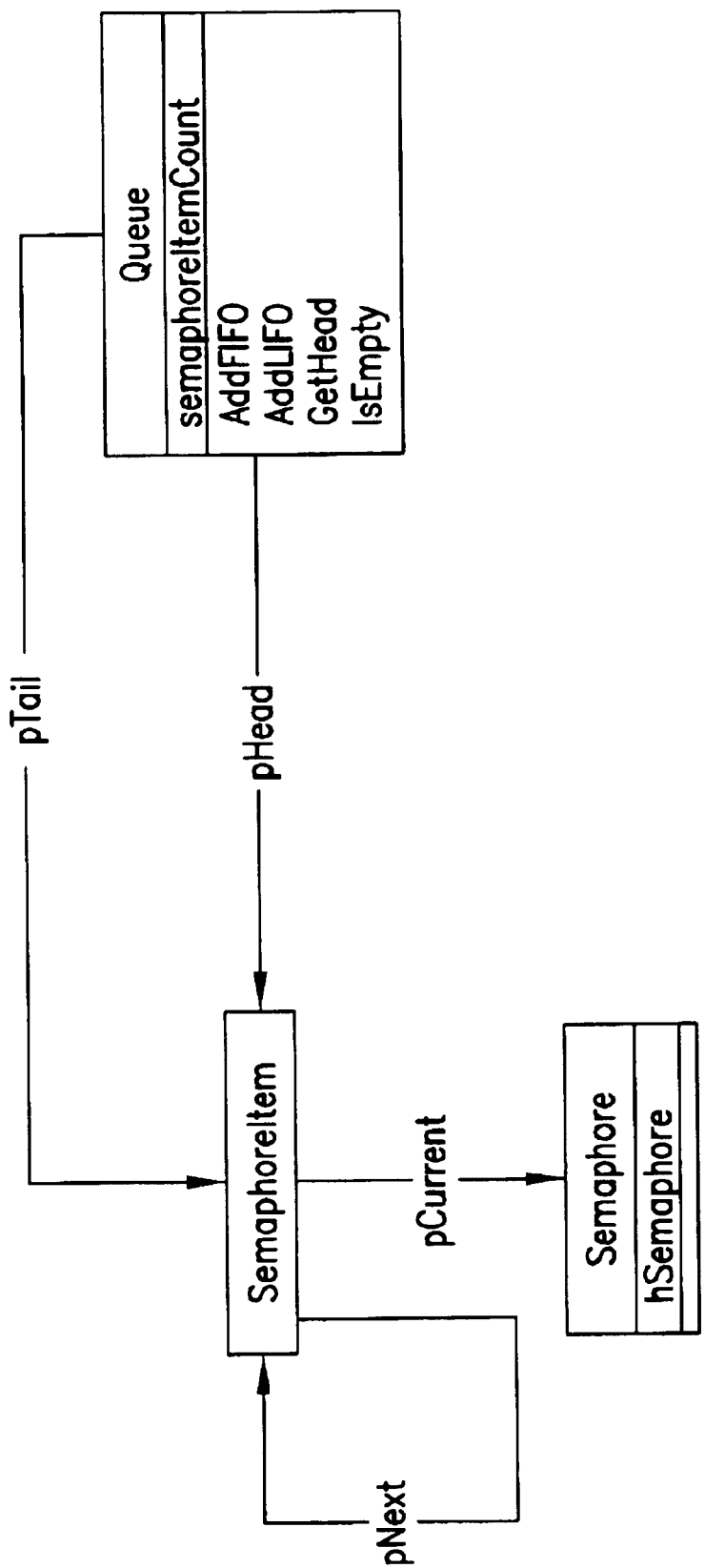
FIG. 9B illustrates one embodiment of a Queue-Semaphore List class.

The pointer pTail is the address of the last SemaphoreItem in the Queue. [Refer to FIG. 9A and 9B]

Attributes:

semaphoreItemCount—The number of SemaphoreItem objects referenced by the Queue.

Operations:

AddFIFO—Adds a new SemaphoreItem to the end of the Queue. By adding the SemaphoreItem to the tail of the Queue, FIFO behavior is achieved.

AddLIFO—Adds a new SemaphoreItem to the head of the Queue. By adding the SemaphoreItem to the head of the Queue, LIFO behavior is achieved.

GetHead—Returns the first SemaphoreItem object in the Queue and deletes the returned SemaphoreItem object from the Queue. When all SemaphoreItem objects have been deleted, this method returns NIL.

Class Name: BinarySemaphore

A BinarySemaphore controls thread access to the HostFrameBuffer and it has an internal counter. The range of this internal count is from zero to one.

Figure 10B:
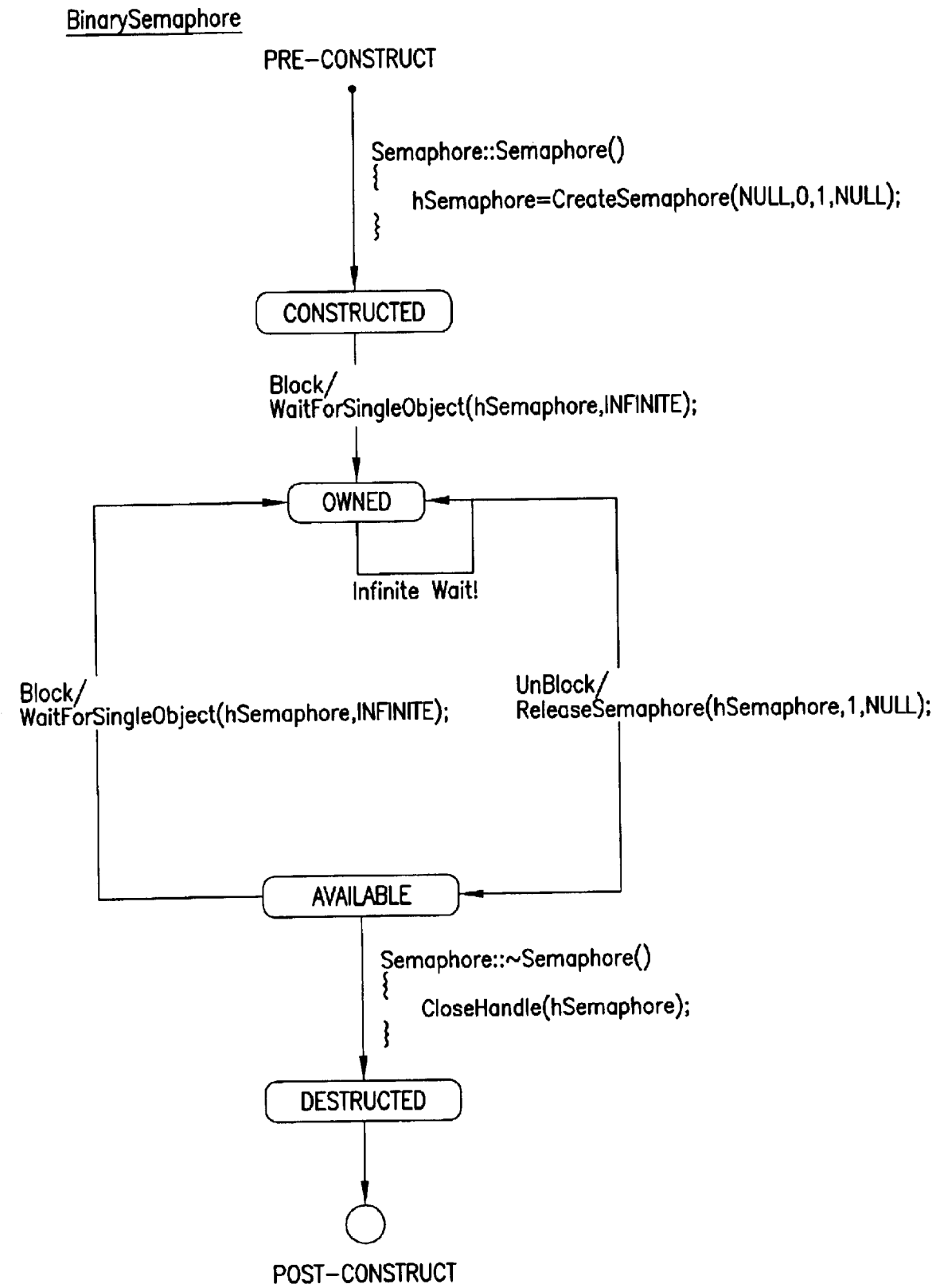
FIG. 10B illustrates an exemplary state diagram for the BinarySemaphore class.

Attribute:

hSemaphore—handle to Semaphore provided by operating system. [Refer to FIG. 10A]

Associations:

A BinarySemaphore class is derived from the superclass Semaphore. [Refer to FIG. 10A]

State:

The BinarySemaphore has two states: AVAILABLE or OWNED. A signaled semaphore means AVAILABLE. A not-signaled semaphore means OWNED. [Refer to FIG. 10B]

Operations:

Block—Gains access to the shared resource. If the wait operation is successful the semaphore count decrements and it is then safe to access the OWNED HostFrameBuffer resource. If the BinarySemaphore internal count is greater than zero, a wait operation on the semaphore succeeds, and its count decrements.

Unblock—When the Thread is finished executing it increments the Semaphore count to indicate the Semaphore is AVAILABLE. If the BinarySemaphore count is zero, then any threads waiting are blocked until the thread who owns the Monitor releases ownership.

I claim:

1. A software system executing on a server of a semiconductor microscopy system in which a video signal generated by a microscope is digitized by a video capture system and communicated to a plurality of remote computing systems comprising:

a producer software module to retrieve the digitized video signal generated by the video capture system, wherein producer software module stores the digitized video signal within a software frame buffer;

a consumer software module to retrieve the digitized video signal from the software frame buffer and to process the digitized video signal for communication to one or more remote computing systems; and a software synchronization mechanism to synchronize access to the frame buffer by the producer software module and consumer software modules.

2. The software system of claim 1, wherein the software system is implemented with object-oriented software.

3. The software system of claim 1, wherein the consumer software module compresses the digitized video signals.

4. The software system of claim 3, wherein the consumer software module inserts the compressed digitized video signals into a database.

5. The software system of claim 1, wherein the consumer software module compares a predefined threshold to statistical data of the processed digitized video signal in order to detect a change from a first frame to a successive frame.

6. The software system of claim 3, wherein the consumer software module retransmits a previously broadcast frame when the statistical data is below the predefined threshold.

7. A system for inspecting a wafer using a plurality of remote computing systems comprising:

a computer comprising a processor, a memory, and a computer-readable medium operatively coupled together;

an operating environment executed by the processor from the computer-readable medium;

a video capture card coupled to the computer to digitize video signals generated by a microscope; and a pair of producer and consumer software modules executing on the processor from the computer-readable medium, wherein the producer software module retrieves digitized video data from the video capture card and communicates the digitized video data to the consumer software module for communication to the remote computing systems.

8. The system of claim 7, wherein the producer and consumer software modules are implemented with object-oriented software.

9. The system of claim 7, wherein the consumer software module compresses the digitized video signals.

10. The system of claim 7, wherein the consumer software module processes the digitized video signal and compares a predefined threshold to statistical data of the processed digitized video signal in order to detect a change from a first frame to a successive frame.

11. The system of claim 10, wherein the consumer software module retransmits a previously broadcast frame to the remote client computers when the statistical data is below the predefined threshold.

12. A set of application program interfaces embodied on a computer-readable medium for execution on a server of a semiconductor microscopy system in which a video signal generated by a microscope is digitized by a video capture system and communicated to a plurality of remote client computers comprising:

a first interface to retrieve the digitized video signal generated by the video capture system and to store the digitized video signal within a software frame buffer; and a second interface to retrieve the digitized video signal from the software frame buffer and to process the digitized video signal for communication to the remote client computers.

13. The set of application program interfaces of claim 12, wherein the second interface causes the server to stream the video signal to the remote client computers.

14. The set of application program interfaces of claim 12, wherein the second interface causes the server to communicate the digitized video signal over a wide area network.

15. The set of application program interfaces of claim 12, wherein the second interface causes the server to communicate the digitized video signal over the Internet.

16. The set of application program interfaces of claim 12, wherein the second interface causes the server to:

compare a predefined threshold to statistical data of the processed digitized video signal in order to detect a change from a first frame to a successive frame; and retransmit the first frame instead of the successive frame as a function of the comparison.

17. The set of application program interfaces of claim 12, wherein the set of application program interfaces conforms to the Component Object Model (COM).

18. A software system executing on a server of a semiconductor microscopy system in which a video signal generated by a microscope is digitized by a video capture system and communicated to a plurality of remote computing systems comprising:

a producer software module to retrieve the digitized video signal generated by the video capture system, wherein the producer software module stores the digitized video signal within a software frame buffer, wherein the producer software module is adapted to receive remote commands and remotely control the video capture system;

a consumer software module to retrieve the digitized video signal from the software frame buffer and to process the digitized video signal for communication to one or more remote computing systems; and a software synchronization mechanism to synchronize access to the frame buffer by the producer software module and consumer software modules.

19. The software system of claim 18, wherein the producer software module is adapted to receive electronic commands over a network from at least one client.

20. The software system of claim 18, wherein the consumer software module is adapted to compare successive video image frames.

21. The software system of claim 20, wherein the consumer software module only transmits the successive image with a change being detected during comparison of successive video image frames.

22. The software system of claim 20, wherein the consumer software module continues to transmit a previous video image frame with no change detected.

23. A software system executing on a server of a semiconductor microscopy system in which a video signal generated by a microscope is digitized by a video capture system and communicated to a plurality of remote computing systems comprising:

a producer software module to retrieve the digitized video signal generated by the video capture system, wherein producer software module stores the digitized video signal within a software frame buffer;

a consumer software module to retrieve the digitized video signal from the software frame buffer and to process the digitized video signal for communication to one or more remote computing systems, wherein the consumer software module compresses the digitized video signal, inserts the compressed digitized video signal into a database, compares a predefined threshold to statistical data of the processed digitized video signal in order to detect a change from a first frame to a successive frame, and retransmits a previously broadcast frame when the statistical data is below the predefined threshold; and a software synchronization mechanism to synchronize access to the frame buffer by the producer software module and consumer software modules.

24. A software system executing on a server of a semiconductor microscopy system in which a video signal generated by a microscope is digitized by a video capture system and communicated to a plurality of remote computing systems comprising:

a producer software module implemented with object-oriented software to retrieve the digitized video signal generated by the video capture system, wherein producer software module stores the digitized video signal within a software frame buffer;

a consumer software module implemented with object-oriented software to retrieve the digitized video signal from the software frame buffer and to process the digitized video signal for communication to one or more remote computing systems, wherein the consumer software module compresses the digitized video signal, inserts the compressed digitized video signal into a database, compares a predefined threshold to statistical data of the processed digitized video signal in order to detect a change from a first frame to a successive frame, and retransmits a previously broadcast frame when the statistical data is below the predefined threshold; and a software synchronization mechanism implemented with object-oriented software to synchronize access to the frame buffer by the producer software module and consumer software modules.

25. The system of claim 1, wherein the producer software module stores the digitized video signal representing one progressive scan of one of a scanning electron microscope and a scanning tunneling microscope.

26. The system of claim 1, wherein, the consumer software module to process the digitized video signal for communication to one or more remote computing systems is adapted to process the digitized video signal into an advanced streaming format.

27. The system of claim 1, wherein the software synchronization mechanism is adapted to ensure that write operations and read operations are performed mutually exclusively.

28. The system of claim 1, wherein the producer software module operates a plurality of producer threads.

29. The system of claim 28, wherein the consumer software module operates a plurality of consumer threads.

30. The system of claim 29, wherein the software synchronization mechanism dynamically at run-time schedules processing of the producer threads and the consumer threads.

31. The system of claim 30, wherein the number of producer threads is equal to the number of consumer threads.

32. The system of claim 30, wherein the number of producer threads is equal to a number of the frame buffers.

33. The system of claim 30, wherein the number of producer threads is equal to a number of microscopes connected to a video capture system.

* * * * *